(12) United States Patent
Freer et al.

(10) Patent No.: US 10,198,958 B2
(45) Date of Patent: Feb. 5, 2019

(54) METHOD AND APPARATUS FOR TRAINING A TEAM BY EMPLOYING BRAINWAVE MONITORING AND SYNCHRONIZED ATTENTION LEVELS OF TEAM TRAINEES

(75) Inventors: Peter A. Freer, Fletcher, NC (US); Stephen J. Scanzoni, Asheville, NC (US)

(73) Assignee: Freer Logic, Skyland, NC (US)

( * ) Notice: Subject to any disclaimer, the term of this patent is extended or adjusted under 35 U.S.C. 154(b) by 3311 days.

(21) Appl. No.: 12/112,528

(22) Filed: Apr. 30, 2008

(65) Prior Publication Data

US 2008/0275358 A1 Nov. 6, 2008

Related U.S. Application Data

(60) Provisional application No. 60/927,703, filed on May 4, 2007.

(51) Int. Cl.

| | |
|---|---|
| *A61B 5/0476* | (2006.01) |
| *A61B 5/0482* | (2006.01) |
| *G09B 19/00* | (2006.01) |
| *G09B 23/28* | (2006.01) |
| *G06F 15/18* | (2006.01) |
| *G06F 17/00* | (2006.01) |
| *G09B 25/00* | (2006.01) |
| *G09B 7/02* | (2006.01) |
| *A61B 5/11* | (2006.01) |
| *A61M 5/172* | (2006.01) |
| *A61N 1/36* | (2006.01) |
| *A61B 5/16* | (2006.01) |
| *A61B 5/00* | (2006.01) |
| *A61B 5/04* | (2006.01) |
| *G06F 19/00* | (2018.01) |
| *A61N 1/05* | (2006.01) |
| *A61B 5/18* | (2006.01) |

(52) U.S. Cl.
CPC .............. *G09B 7/02* (2013.01); *G09B 19/00* (2013.01); *A61B 5/04001* (2013.01); *A61B 5/0476* (2013.01); *A61B 5/0482* (2013.01); *A61B 5/1118* (2013.01); *A61B 5/16* (2013.01); *A61B 5/18* (2013.01); *A61B 5/7285* (2013.01); *A61M 5/1723* (2013.01); *A61N 1/0531* (2013.01); *A61N 1/36139* (2013.01); *G06F 19/00* (2013.01)

(58) Field of Classification Search
CPC ..... A61B 5/0476; A61B 5/165; A61B 5/0022; A61B 5/486; A61B 5/04085; A61B 5/4064; A61B 5/0482; A61B 5/7267; A61B 5/745; A61B 5/0042; A61B 5/168; A61B 5/4035; A61B 5/7214; A61B 5/7275; A61B 6/035; A61B 6/5217; A61B 5/16; A61B 5/18; A61B 5/04001; A61B 5/1118; A61B 5/7285; G06F 19/00; G06F 3/038; G09B 5/00; G09B 7/00; G16H 10/60; A61M 2230/10; A61M 5/1723; A61F 4/00; A63F 2300/60; H04N 21/4126; H04N 21/42201; H04N 21/4307; G01R 33/4806; G06T 2203/30004; A61N 1/36139; A61N 1/0531

See application file for complete search history.

(56) References Cited

U.S. PATENT DOCUMENTS

| | | |
|---|---|---|
| 3,877,466 A | 4/1975 | Montor |
| 4,008,714 A | 2/1977 | Silva |
| 4,203,452 A | 5/1980 | Cohen |
| 4,332,566 A | 6/1982 | Mazeski |
| 4,358,118 A | 11/1982 | Plapp |
| 4,461,301 A | 7/1984 | Ochs |
| 4,630,817 A | 12/1986 | Buckley |
| 4,683,891 A | 8/1987 | Cornellier |
| 4,751,642 A | 6/1988 | Silva |
| 4,812,126 A | 3/1989 | Gilliksen |
| 4,926,969 A | 5/1990 | Wright |
| 4,928,704 A * | 5/1990 | Hardt ............................ 600/545 |
| 4,949,726 A | 8/1990 | Hartzell |
| 4,955,388 A | 9/1990 | Silberstein |
| 5,001,632 A | 3/1991 | Hall-tipping |
| 5,213,338 A | 5/1993 | Brotz |
| 5,339,826 A | 8/1994 | Schmidt |

(Continued)

FOREIGN PATENT DOCUMENTS

| | | |
|---|---|---|
| EP | 0270535 B1 | 3/1993 |
| EP | 0674927 A1 | 10/1995 |

(Continued)

OTHER PUBLICATIONS

International Search Report dated Jun. 4, 2009 in corresponding application PCT/US08/62215; WO 2008/137542.

*Primary Examiner* — Chang-Yu Wang
(74) *Attorney, Agent, or Firm* — Luedeka Neely Group, P.C.; Steve Schnedler; Rick Barnes

(57) ABSTRACT

Training methods and apparatus wherein a training environment is activated only when a trainee is in a focused attention state. A brainwave monitor is employed for determining level of attention. The training environment is activated when the level of attention of the trainee is at or above a predetermined attention threshold. Activation of the training environment provides feedback to the trainee that he or she is in a focused attention state, and at the same time provides the incentive to remain in the focused attention state. A focused attention state is important if not required for training/learning success. The method and apparatus may be employed for training individual trainees, as well as for training team member trainees.

4 Claims, 32 Drawing Sheets

(56) References Cited

U.S. PATENT DOCUMENTS

| | | |
|---|---|---|
| 5,343,871 A | 9/1994 | Bittman |
| 5,362,049 A | 11/1994 | Hofer |
| 5,377,100 A | 12/1994 | Pope |
| 5,406,957 A | 4/1995 | Tansey |
| 5,460,184 A | 10/1995 | Sato |
| 5,470,081 A | 11/1995 | Sato |
| 5,571,057 A | 11/1996 | Ayers |
| 5,601,435 A | 2/1997 | Quy |
| 5,662,117 A | 9/1997 | Bittman |
| 5,692,517 A | 12/1997 | Junker |
| 5,724,987 A | 3/1998 | Gevins |
| 5,740,812 A | 4/1998 | Cowan |
| 5,762,611 A | 6/1998 | Lewis |
| 5,772,508 A | 6/1998 | Sugita |
| 5,899,867 A | 5/1999 | Collura |
| 5,911,581 A | 6/1999 | Reynolds |
| 5,983,129 A | 11/1999 | Cowan |
| 6,012,926 A | 1/2000 | Hodges |
| 6,026,322 A | 2/2000 | Marcelo |
| 6,057,846 A | 5/2000 | Sever, Jr. |
| 6,097,981 A | 8/2000 | Freer |
| 6,175,762 B1 | 1/2001 | Kirkup |
| 6,183,259 B1 | 2/2001 | Macri |
| 6,254,536 B1 | 7/2001 | Devito |
| 6,349,231 B1 | 2/2002 | Musha |
| 6,402,520 B1 | 6/2002 | Freer |
| 6,434,419 B1 | 8/2002 | Gevins |
| 6,450,820 B1 | 9/2002 | Palsson |
| 6,457,975 B1 * | 10/2002 | Miranda et al. .............. 434/236 |
| 6,625,485 B2 | 9/2003 | Levendowski |
| 6,626,676 B2 | 9/2003 | Freer |
| 6,685,652 B1 | 2/2004 | Teicher |
| 6,688,889 B2 | 2/2004 | Wallace |
| 6,699,043 B2 | 3/2004 | Ho |
| 6,722,888 B1 | 4/2004 | Macri |
| 6,829,502 B2 | 12/2004 | Hong |
| 6,947,790 B2 | 9/2005 | Gevins |
| 6,952,809 B2 | 10/2005 | Beranek |
| 6,996,261 B2 | 2/2006 | deCharms |
| 7,043,193 B1 * | 5/2006 | Vashi et al. .................... 434/353 |
| 7,120,880 B1 | 10/2006 | Dryer |
| 7,162,295 B2 | 1/2007 | Ryu |
| 7,177,676 B2 | 2/2007 | Setiabudi |
| 7,234,943 B1 | 6/2007 | Aleali |
| 7,331,870 B2 | 2/2008 | Smith |
| 7,594,815 B2 * | 9/2009 | Toly .............................. 434/262 |
| 2002/0077534 A1 | 6/2002 | DuRousseau |
| 2002/0086272 A1 | 7/2002 | Ho et al. |
| 2002/0140633 A1 * | 10/2002 | Rafii et al. ........................ 345/8 |
| 2003/0136900 A1 * | 7/2003 | Shechter et al. ............ 250/222.1 |
| 2004/0076934 A1 * | 4/2004 | Wen et al. ..................... 434/157 |
| 2004/0191747 A1 | 9/2004 | Atsumori |
| 2004/0230549 A1 | 9/2004 | Freer |
| 2005/0125150 A1 * | 6/2005 | Wang et al. .................. 701/213 |
| 2005/0195165 A1 * | 9/2005 | Mitchell ....................... 345/158 |
| 2006/0290663 A1 * | 12/2006 | Mitchell ....................... 345/156 |
| 2007/0031798 A1 | 2/2007 | Gottfried |
| 2008/0208468 A1 * | 8/2008 | Martin ......................... 701/213 |

FOREIGN PATENT DOCUMENTS

| | | |
|---|---|---|
| EP | 0632421 B1 | 12/1998 |
| EP | 1512370 A1 | 3/2005 |

* cited by examiner

METHOD AND APPARATUS FOR TRAINING A TEAM BY EMPLOYING BRAINWAVE MONITORING AND SYNCHRONIZED ATTENTION LEVELS OF TEAM TRAINEES

CROSS-REFERENCE TO RELATED APPLICATION

The benefit of U.S. provisional patent application Ser. No. 60/927,703, filed May 4, 2007, is claimed.

BACKGROUND OF THE INVENTION

The invention relates in general to human performance training (HPT) and, more particularly, to training environments implementing computer-guided training, with or without an instructor.

Corporate, military, athletic, medical, and academic arenas have placed greater emphasis on human performance training (HPT) more now than ever before in history. HPT may be comprised of cognitive, behavioral, psychomotor, or emotional skill sets. HPT is frequently expensive and time consuming, and often ineffective.

Many times, as evidenced in the nuclear power industry, a team effort is necessary to resolve a problem or simply carry on designated duties. A great deal of time and money are spent on team-based training. Traditionally, nuclear industry training, as an example, has concentrated mainly on the development of the technical skills and performance of the individual technician. Indeed, both researchers and practitioners suggest that more emphasis should be placed on the performance of the crew as a team and on factors that affect crew coordination and teamwork. Teams of people perform duties, yet training often remains focused on individual responsibilities. Training a team presents similar problems to training an individual. Additionally issues of collaboration, cohesion, task distribution, and group cognition are encountered. An accepted view is that it is the team, not the nuclear power station or the individual technician, that is at the root of most accidents and incidents.

SUMMARY OF THE INVENTION

In one aspect, a training method for training a trainee is provided. The training method includes employing a brainwave monitor for determining level of attention, providing a training environment, and monitoring the level of attention of the trainee and activating the training environment when the level of attention of the trainee is at or above a predetermined attention threshold.

In another aspect, a training method for training a team including at least two team member trainees is provided. The training method includes employing brainwave monitors for determining level of attention for each team member trainee; providing a training environment, and monitoring the levels of attention of the team member trainees and activating the training environment when the level of attention of at least one team member trainee is at or above a predetermined attention threshold.

In yet another aspect, apparatus for training a trainee is provided. The apparatus includes a training environment; a brainwave monitor for monitoring electrical activity within the brain of the trainee, and determining the level of attention of the trainee; and an activation device connected to the brainwave monitor and to the training environment, and operable to activate the training environment when the determined level of attention of the trainee is at or above a predetermined attention threshold.

In still another aspect, apparatus for training a team including at least two team member trainees is provided. The apparatus includes a training environment; a brainwave monitor for each trainee for monitoring electrical activity within the brain of each trainee, and determining each trainee's level of attention; and an activation device connected to the brainwave monitors and to the training environment, and operable to activate the training environment when the level of attention of at least one team member trainee is at or above a predetermined attention threshold.

DETAILED DESCRIPTION

Embodiments of the invention provide training methods and corresponding apparatus wherein training programs conducted in a training environment are combined with attentional brainwave monitoring to utilize neuroplasticity for the enhancement of human performance in both individual and team training.

Human performance training (HPT) performed via computer guided training, instructor guided training, or a combination of the two modalities, attempts to teach subjects to enhance personal performance. Although moderate gains in ability have been produced historically, the general applicability of this approach has been significantly limited by inadequate attention by the trainee to the trainer, the training materials, or both.

In order to assimilate new information, strategies, or skills and store them in long-term memory, sufficient attention must be given the stimuli provided by the trainer or training materials. Similar to the weaknesses in neurofeedback (NF) training, critics cite lack of transfer, generalization, and permanence of the presented skills back to the workplace.

Figure 1A:
FIG. 1A is a prior art illustration of a trainee undergoing training in a computer lab for his vocation, but unable to maintain attention to the materials presented.
Figure 1B:
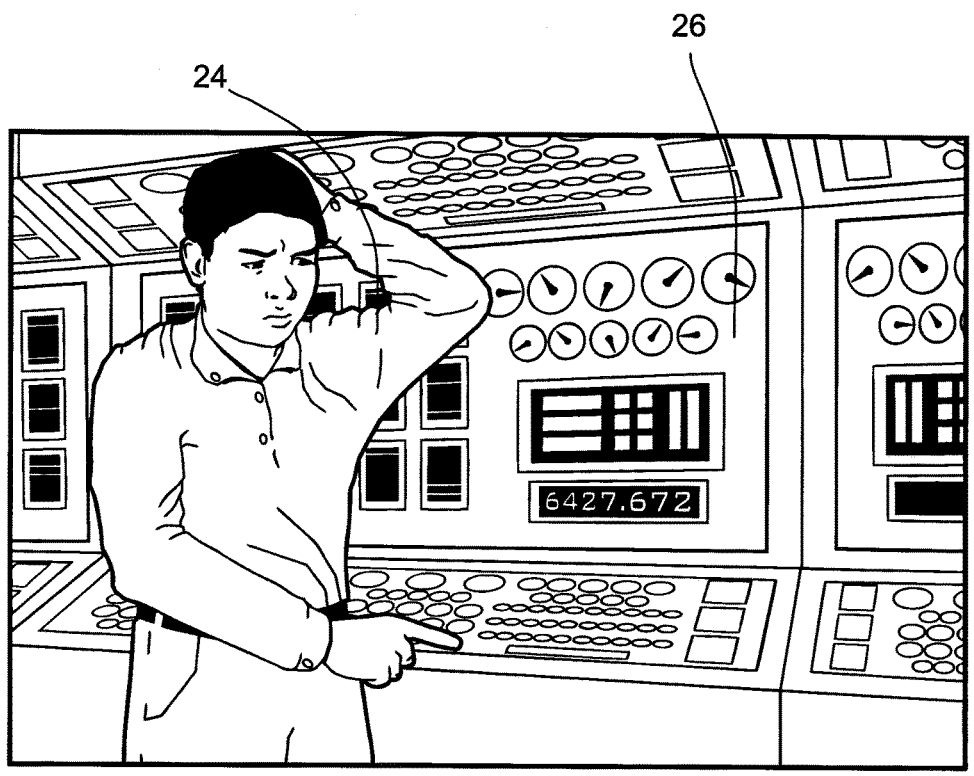
FIG. 1B is a prior art illustration of a trainee returning to a workplace environment, but unable to remember and transfer skills that were presented during previous training.

As prior art examples of individuals, FIG. 1A illustrates a trainee 20 undergoing training in a computer lab for his vocation, but unable to maintain attention to the materials presented on a control panel 22 because the trainee 20 is daydreaming. FIG. 1B illustrates a trainee 24 returning to the workplace environment represented by a control panel 26, but unable to remember and transfer skills that were presented during previous training, as indicated by a head scratch.

Although individuals trained in team issues may understand the benefits of team training, teams often fail as a whole due to the failure of just one team member. The lack of attention or engagement of one or more team members can negatively affect the entire team's performance. Developing shared situational awareness and team cognition is essential to overall team function.

Figure 2A:
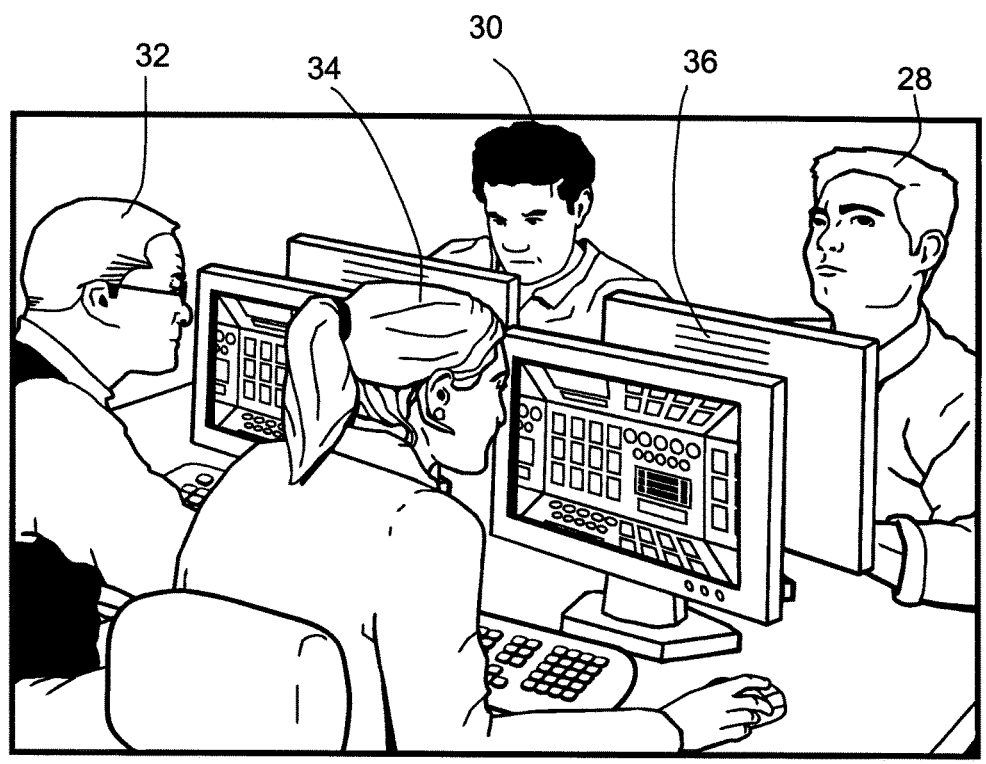
FIG. 2A is a prior art illustration of a trainee undergoing training in a computer lab for his vocation with his colleagues, but unable to maintain attention to the materials presented.
Figure 2B:
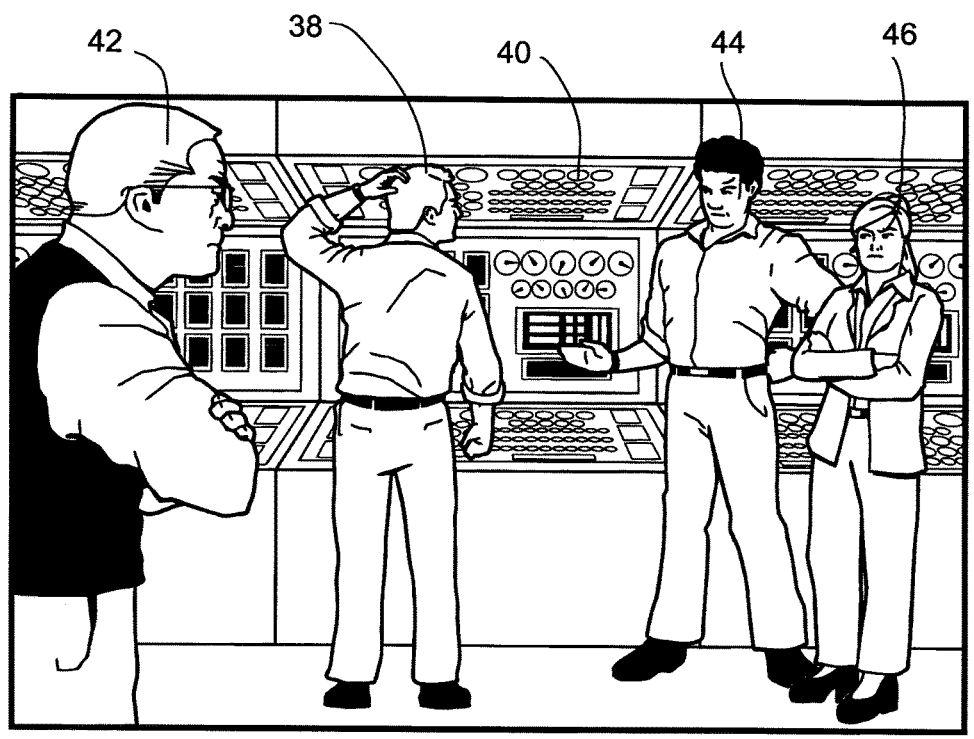
FIG. 2B is a prior art illustration of a trainee returning to a workplace environment, but unable to remember and transfer skills that were presented during previous training, while colleagues become frustrated.

As prior art examples of team training issues, FIG. 2A illustrates a trainee 28 undergoing training in a computer lab for his vocation with his colleagues 30, 32 and 34, but unable to maintain attention to the materials presented, represented by a control panel 36, because the trainee 28 is daydreaming. FIG. 2B illustrates a trainee 38 returning to the workplace environment represented by a control panel 40, but unable to remember and transfer skills that were presented during previous training, as indicated by a head scratch, while colleagues 42, 44 and 46 become frustrated.

Physical brain changes occur whenever we learn or experience something new. This ability of the brain to revise and reorganize itself with learning is termed neuroplasticity, and perpetuates throughout an individual's lifetime.

However, brains do not reorganize casually, easily, or arbitrarily. Maintaining a highly focused attention state is hard work. For a new skill to be learned (both acquired and maintained), a trainee must be engaged and progressively challenged. Training should be intensive repetitive. Above all, sharply focused attention is necessary. Without focused attention or concentration, learning does not occur. It is the act of actively and willfully focusing attention during the learning process that actually causes neuronal changes in the function of the brain.

Prior to the subject invention, the active engagement of a focused attention state required for a training/learning success has been problematic.

Training methods and apparatus embodying the invention employ brainwave monitoring effectively and actively engage and utilize the level of attention of a trainee throughout the entire learning/training process. Methods and apparatus embodying the invention are applicable for both individuals and teams (corporate, academic, industrial, medical, athletics, governmental, etc.) in a variety of training environments and modes (e-learning, simulators, games, classroom, VR, etc.)

The term electroencephalography (EEG) is generally employed to refer to the measurement of electrical activity produced by the brain as measured or recorded from electrodes placed on the scalp of a person. Such activity is commonly termed "brain wave" activity. (The related term electroencephalogram refers to a graphic record produced by an electroencephalograph.) The resultant electrical signals from the electrodes are correspondingly termed EEG signals or brain wave signals, and are based on the electrical activity within the brain of a person. Scientists studying the brain have found that EEG or brain wave signals include a number of components, including signals resulting from rhythmic activity falling within a number of frequency bands. Three brainwave frequency bands in particular have been recognized as characteristically distinguishing various states of attention and vigilance. Beta wave (approximately 12-16 Hz) activity has been observed for vigilant states. Alpha wave (approximately 8-13 Hz) activity predominates in alert and relaxed states. Theta wave (approximately 4-8 Hz) activity rises as attention lapses. As examples, EEG-based biofeedback is employed in attention training, as is disclosed for example in Freer U.S. Pat. No. 6,097,981 titled "Electroencephalograph Based Biofeedback System and Method" and in Freer U.S. Pat. Nos. 6,402,520 and 6,626,676 titled "Electroencephalograph Based Biofeedback System For Improving Learning Skills." EEG-based biofeedback employed in computerized training apparatus is disclosed in Freer et al Patent Application Pub. No. US 2004/0230549 titled "Systems and Methods for Behavioral Modification and Behavioral Task Training Integrated with Biofeedback and Cognitive Skills Training." As a more particular example, Freer U.S. Pat. No. 6,097,981 discloses detecting the energy levels corresponding to the alpha, beta, and theta frequency bands as an indication of the attention level of the user.

In a typical implementation, brain wave signals are bandpass-filtered to determine signal magnitude within at least one of the relevant frequency bands. Typically an RMS-to-DC converter or other RMS converter follows a bandpass filter. The determined magnitude is employed as an indicator of the level of attention of an individual. Particularly useful are theta waves (4 Hz to 8 Hz). A decrease in the magnitude of theta waves is indicative of an increasing level of attention. A threshold or baseline may be employed to determine a binary "yes" or "no" signal as an indication of whether a person is in an attentive state or not. In the example of theta waves, a magnitude below the threshold or baseline indicates an attention level above an attention baseline.

Figure 3:
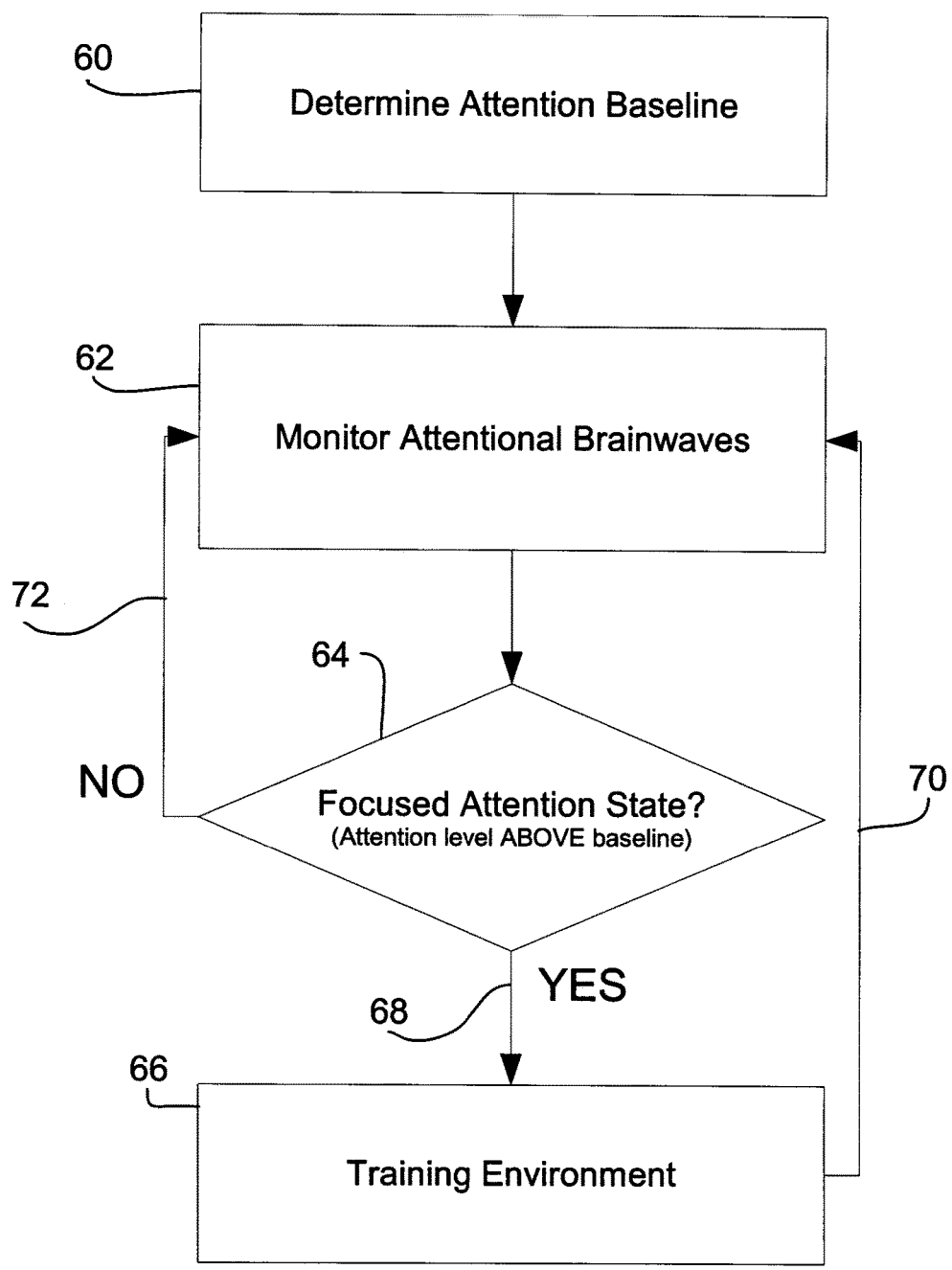
FIG. 3 is a flowchart representing embodiments of the invention.

FIG. 3 is a flowchart representing an embodiment of the invention in overview. FIG. 3 is applicable to embodiments of the invention for training individual trainees, as well as for training teams including at least two team member trainees. FIG. 3 in part represents software executing in a computer, and thus in part is a program flowchart. More detailed examples are described hereinbelow with reference to other drawing FIGURES illustrating trainees both individually and in teams.

Considering FIG. 3 in detail, as represented in box 60, before a trainee enters a training environment or exercise, attentional brainwaves are monitored to determine an attention baseline. Thus, the individual first participates in a short computer-mediated task or exercise that requires a high level of concentration to complete successfully. The trainee may be either an individual trainee, or a team member trainee. During this short exercise, electrical activity within the brain is monitored, using a brainwave monitor. Brain wave signals are bandpass-filtered to determine signal magnitude within at least one of the relevant frequency bands, referred to herein as attentional brainwaves. This determined magnitude, indicating the level of attention of an individual, is established as an attention threshold or attention baseline, also referred to herein as a predetermined attention threshold. (Again, the relationship between signal magnitude within one of the relevant frequency bands and level of attention may be an inverse one. For example, a decrease in the magnitude of theta waves is indicative of an increasing level of attention. Description herein of levels of attention and comparison to attention baselines refers to the interpreted level of attention, and not necessarily absolute signal magnitude within a relevant brainwave frequency band.) The result may be viewed as a snapshot of the brain activity of the trainee while concentrating, and represents the focused attention baseline, or threshold activity figure, with reference to attentional brainwaves. Attention baseline establishment is highly individual, and accordingly is likely to be different from that of other trainees. Moreover, the attention baseline of an individual may change over time. Even so, although not presently preferred, the invention may be embodied in methods and apparatus where a common attention baseline is employed for a plurality of team members.

During the subsequent training activity or exercise, the electrical activity within the brain of each trainee continues to be monitored, as represented by a program loop including box 62 where attentional brainwaves are monitored, decision box 64 where it is determined based on brainwave activity whether individual trainees are maintaining focused attention states, and box 66 which represents a training environment an individual trainee or team member trainees are allowed to enter only if he, she or they are maintaining a focused attention state or focused attention states. In monitoring box 62, depending on whether an individual trainee is being trained, or a team including at least two team member trainees, attentional brainwave activity of one or more trainees is monitored.

In embodiments where an individual trainee is being trained, in decision box 64, attentional brainwave activity indicating a level of attention at or above the established attention baseline (or threshold) for the individual trainee indicates the individual is operating in his or her focused attention state. The decision is "yes," and branch 68 is taken. Accordingly, if the trainee is in a focused attention state, the trainee is allowed to actively participate in the training environment or exercise represented by box 66. In other words, the training environment 66 is activated. Even so, as part of the continuous monitoring, as indicated by line 70, program execution loops from box 66 back to box 62, where attentional brainwaves are again monitored.

Conversely, in box 64, attentional brainwave activity indicating a level of attention below the established attention baseline for the individual trainee indicates the individual has lost focus. The decision is "no," and branch 72 is taken back to box 62. The trainee is not allowed to proceed to the training environment represented by box 66. In other words, the training environment 66 is not activated. A wait loop is in effect established, until such time as the trainee regains a focused attention state.

Activation of the training environment 66 provides feedback to the trainee that he or she is in a focused attention state, and at the same time provides the incentive to remain in the focused attention state. Additionally, in certain training environments, particular interactive elements may be made available for selection and actuation. The act of selecting and actuating elements in the training environment serves to further reinforce the high focused attention state and ensure active participation in the actual learning process.

In embodiments where a team including at least two team member trainees is being trained, there are two alternatives, which may be viewed as "individual" or "collective," depending on the training protocol for a particular training session. In both cases, the attentional brainwaves or levels of attention of all team member trainees are monitored. In an "individual" protocol, the training environment 66 is activated when the level of attention of at least one team member trainee is at or above a predetermined attention threshold, which is the attention baseline for the particular team member trainee. In a "collective" protocol, the training environment 66 is activated when the levels of attention of all team member trainees are at or above a predetermined attention threshold, or preferably, when the level of attention of each team member trainee is at or above a predetermined attention threshold for the particular team member trainee, which is the attention baseline for the particular team member trainee.

More particularly, in embodiments where a team including at least two team member trainees is being trained, in decision box 64 it is determined whether at least one team member trainee or all team member trainees are in a focused attention state, depending on whether the protocol is "individual" or "collective." If the decision is "yes," branch 68 is taken, and the training environment 66 is activated. Even so, as part of the continuous monitoring, as indicated by line 70, program execution loops from box 66 back to box 62, where attentional brainwaves are again monitored.

Conversely, if in box 64 it is determined that either none or not all of the individual trainees are in a focused attention state, the decision is "no," and branch 72 is taken. The trainees are not allowed to proceed to the training environment represented by box 66. In other words, the training environment 66 is not activated. A wait loop is in effect established, until such time as at least one team member trainee or all team member trainees regain a focused attention state.

Described hereinbelow are several more particular embodiments of the invention. Many variations and combinations are possible, beyond the specific embodiments illustrated and described herein. Accordingly, the embodiments illustrated and described herein are by way of example and not limitation.

FIGS. 3A, 3B, 3C, 3D and 3E illustrate a trainee 100 employing a brainwave monitor generally designated 102. The brainwave monitor 102 more particularly determines level of attention as described hereinabove with reference to FIG. 3, and accordingly may also be termed an attentional brainwave monitor 102. In general, the attentional brainwave monitor 102 is known, as is for example disclosed in the above-referenced Freer U.S. Pat. Nos. 6,097,981, 6,402, 520 and 6,626,676; and Freer et al Patent Application Pub. No. US 2004/0230549. As noted above, in a typical implementation, brain wave signals are bandpass-filtered to determine signal magnitude within at least one of the relevant frequency bands, and this determined magnitude is employed as indicating the level of attention of an individual. A predetermined attention threshold or baseline is employed to determine a binary "yes" or "no" signal as an indication of whether a trainee is in an attentive state or not. However, other approaches to brainwave signal analysis may be employed to recognize when a trainee is in a state of focused attention. The particular analysis approach described herein is by way of example, and not limitation.

In FIGS. 3A, 3B, 3C, 3D and 3E, the attentional brainwave monitor 102 is conventional and includes a sensor headband 104 and a brainwave monitoring device hardware unit 106 attached to a desktop computer 108 or personal computer (PC) 108. The illustrated computer 108 includes a CPU unit 110, a monitor 112, and a mouse 114, as well as speakers (not shown) to output sounds, such as alarm bell distracters. The sensor headband 104 supports sensors such as electrodes against the head of the trainee 100 to produce electrical signals based on electrical activity within the brain of the trainee 100, commonly known as brainwave activity. These electrodes are connected to an input of a suitable amplifier (not shown) within the hardware unit 106. Bandpass filtering, RMS conversion and threshold detection functions to determine whether the trainee 100 is in a focused attention state are performed either by circuitry within the hardware unit 106 or by a combination of circuitry within the hardware unit 106 and the personal computer 108. Thus the required functions may be distributed between the hardware unit 106 and the programmed PC 108 depending on design considerations for a particular system. The attentional brainwave monitor 102 determines that the trainee 100 is in a focused attention state when the level of attention of the trainee 100 is at or above a predetermined attention threshold. The attentional brainwave monitor 102 determines that the trainee 100 is not in a focused attention state when the level of attention of the trainee below the predetermined attention threshold.

In FIGS. 3A, 3B, 3C, 3D and 3E, a training environment 120 corresponding to the FIG. 3 training environment 66 is represented on the computer monitor 112 as a virtual rendition of an industrial control panel 122 including a set of actionable elements 124 representing controls, as examples. In other words, the training environment 120 is an industrial control panel simulator. Also visible on the computer monitor 112 is a mouse pointer 126. The training environment 120 is generated by the computer 108 and programming therein, and is activated when the attentional brainwave monitor 102 determines that the trainee 100 is in a focused attention state. Thus also implemented within the programmed computer 108 is what may be termed an activation device 128 connected to the attentional brainwave monitor 102 and to the training environment 120, and operable to activate the training environment 120 when the determined level of attention of the trainee is at or above a predetermined attention threshold.

Figure 3A:
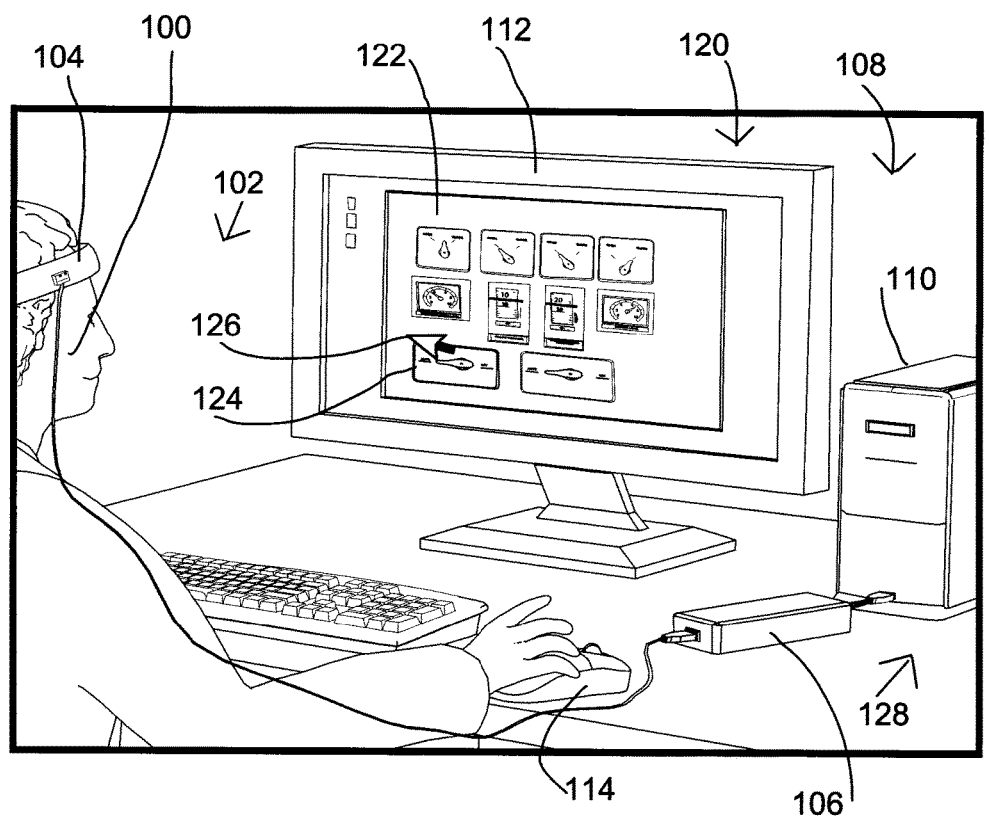
FIG. 3A illustrates a trainee in a training environment represented as an industrial control panel simulator on a personal computer, with monitoring of attentional brainwave activity of the trainee.

In the particular example of FIG. 3A, the trainee 100 is not in a focused attention state.

Figure 3B:
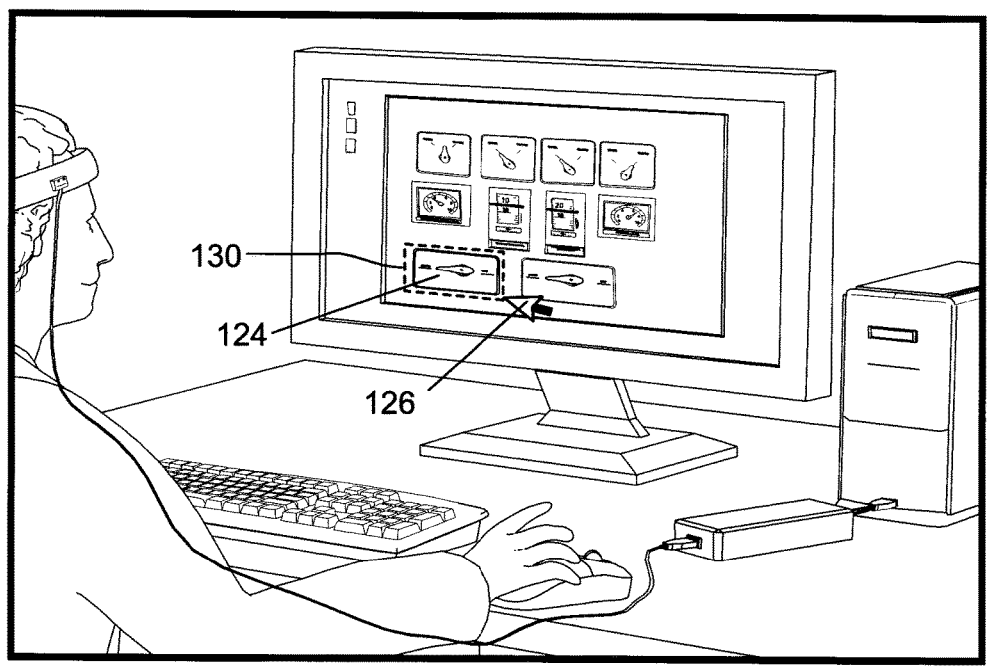
FIG. 3B illustrates an example in a sequence of events where the FIG. 3A trainee is in a focused attention state.

In FIG. 3B, the trainee 100 has reached a focused attention state; the level of attention of the trainee 100 is at or above his predetermined attention threshold or baseline. For training purposes, an advantage is that the trainee 100 is fully paying attention while engaged in the training environment 120, thus ensuring optimal assimilation of data for long-term retention and transfer. As part of the "activation" of the training environment 120, the trainee 100 is permitted to select an actionable element 124 in the training environment 120 using the mouse pointer 126. The selected actionable element 124 is then bounded by a rectangular marquee 130 as a visible indication.

In the example of FIG. 3B, the selection of an actionable element 124 in the training environment 120 is represented by a rectangular marquee 130 and the mouse pointer 126. However, what is illustrated is by way of example and not of limitation, and embodiments of the invention may implement a different selection method.

Figure 3C:
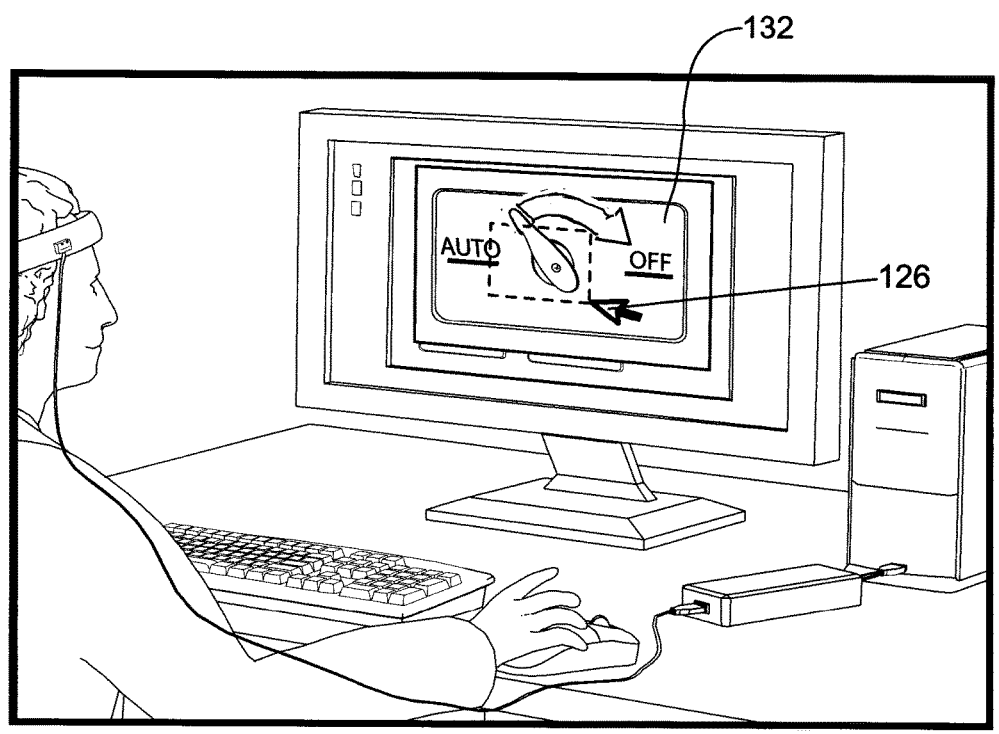
FIG. 3C illustrates an alternative example in a sequence of events where the FIG. 3A trainee is in a focused attention state.

As another example, in FIG. 3C, a selected actionable element 132 is enlarged as a result of the continued focused attention state of the trainee 100. The trainee 100 is permitted to use the mouse 114 and mouse pointer 126 to actuate the actionable element 132, setting the control to a new setting.

Figure 3D:
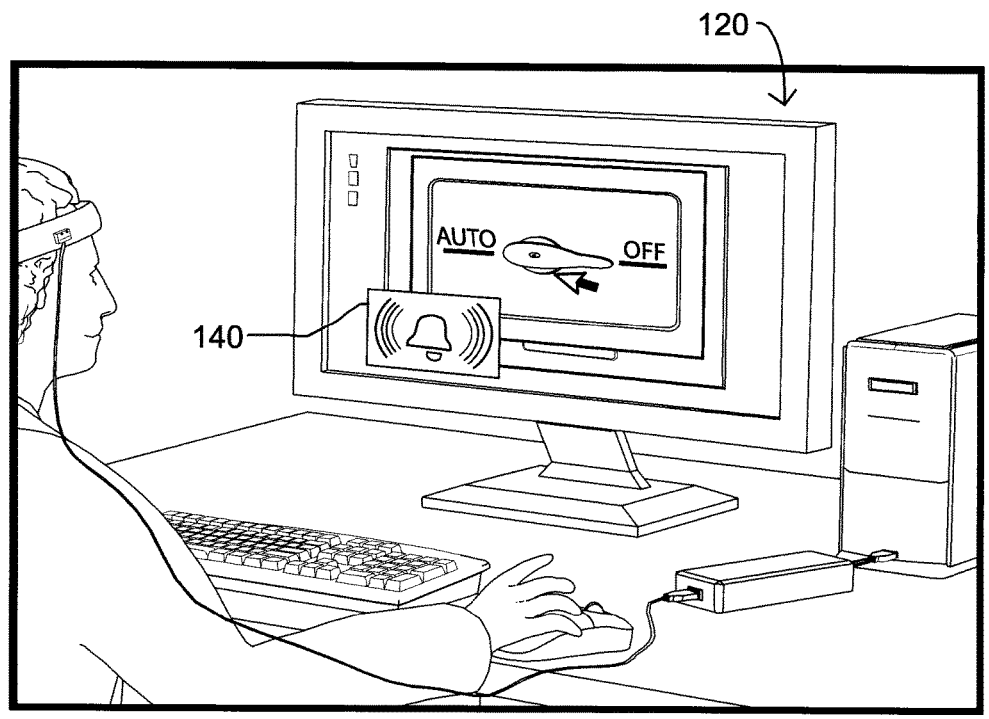
FIG. 3D illustrates a distraction introduced into the FIG. 3A training environment, where the distraction has challenged the trainee to the extent the trainee is no longer in a focused attention state.

FIG. 3D illustrates a distracter or distraction 140 introduced into the training environment 120. The distraction 140 challenges the focused attention state of the trainee 100, and is a combination visual and audible distraction 140 in the particular form of an audible alarm 140, illustrated as a ringing bell 140. In the particular example of FIG. 3D, the trainee 100 is distracted by an audible alarm 140 and is unable to maintain a focused attention state. The attentional brainwave monitor 102 detects the trainee's 100 lack of focused attention. As a result, and as described hereinabove in the context of the FIG. 3 flowchart, the trainee 100 is not permitted to select of actuate the actionable element 132 in the training environment 120. Examples of distracters which may be employed in embodiments of the invention are sounds, characters on a display, a person, tactile stimulation, or extraneous visual elements.

Figure 3E:
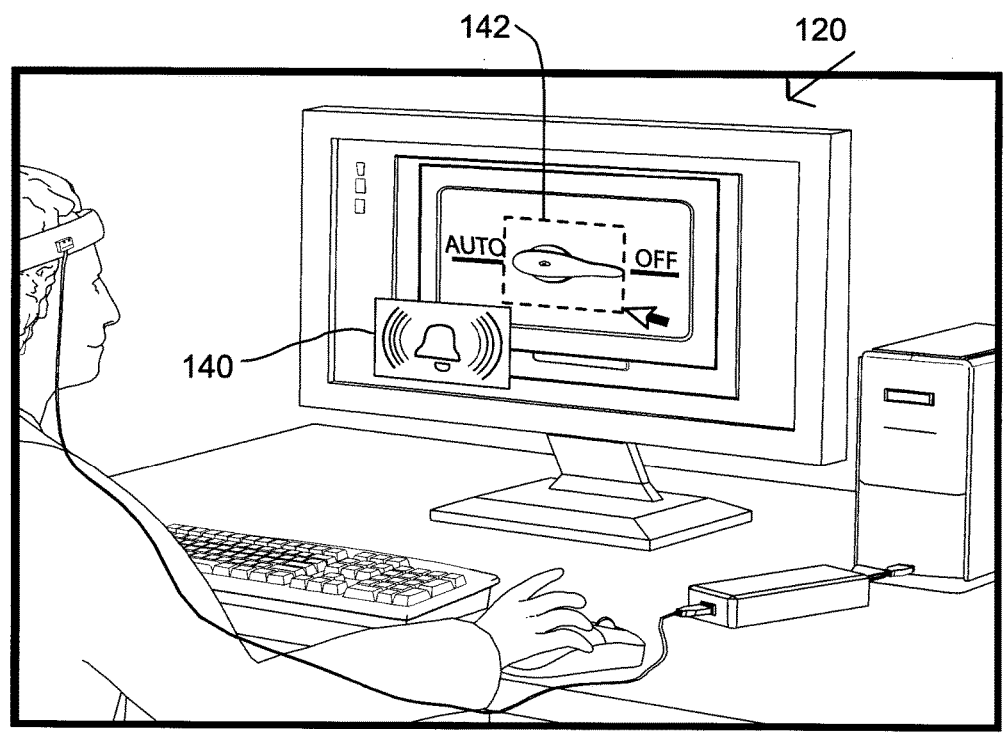
FIG. 3E illustrates a contrasting situation where a distraction is introduced into the FIG. 3A training environment, but the trainee is able to maintain a focused attention state.

FIG. 3E illustrates a contrasting situation. In FIG. 3E, the distraction 140 in the form of the audible alarm 140 likewise has been introduced in the training environment 120. The trainee 100 in FIG. 3E however successfully overcomes the distraction 140 represented by the audible alarm 140 and is able to remain in or reach a focused attention state. As illustrated by a rectangular marquee in FIG. 3E, the training environment is "activated," and the trainee 132 accordingly is permitted to select and actuate the actionable element 132.

In the examples of FIGS. 3A to 3E, the training environment 120 is represented as industrial control panel simulator 122 running on a personal computer 108. This is by way of example and not of limitation. Embodiments of the invention may be implemented in various alternative training environments.

FIGS. 4A, 4B, 4C and 4D illustrate a team 200 of two trainees 202 and 204 engaged in an industrial control panel simulator training environment 206. The trainees 202 and 204 are using respective attentional brainwave monitors 208 and 210, each of which is essentially identical to the attentional brainwave monitor 102 described hereinabove with reference to FIGS. 3A, 3B, 3C, 3D and 3E, and accordingly are not described in detail here. Briefly, the attentional brainwave monitors 208 and 210 include respective sensor headbands 212 and 214 connected to respective brainwave monitoring device hardware units 216 and 218. The hardware units 216 and 218 are connected to a single a desktop computer 220 or personal computer (PC) 220, which includes a CPU unit 222, a mouse 224, and a touch screen computer display 226. Implemented within the programmed computer 220 are functions related to the attentional brainwave monitors 208 and 210, depending on design considerations for a particular system. Also implemented within the programmed computer 220 is an activation device 228 connected to the attentional brainwave monitors 208 and 210 and to the training environment 206, and operable to activate the training environment 206 when the determined level of attention of each team member trainee 202 and 204 is at or above a predetermined attention threshold for the particular team member trainee.

Figure 4A:
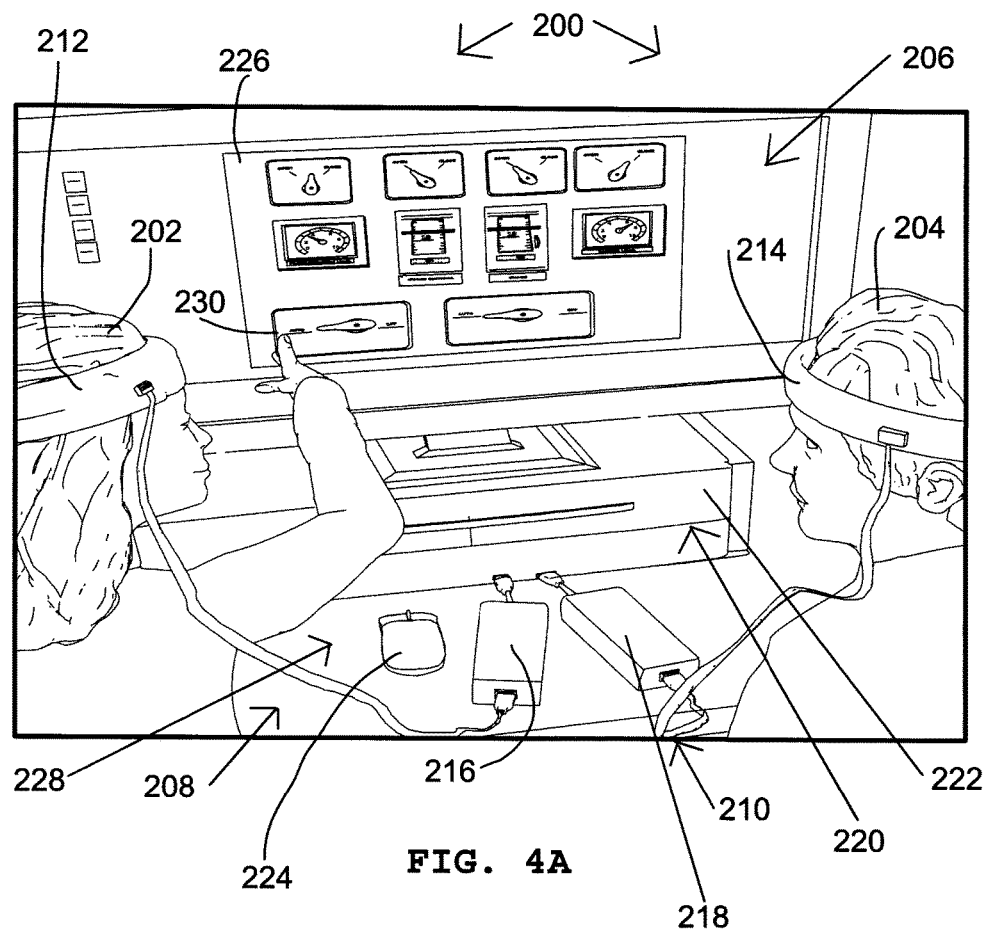
FIG. 4A illustrates a team made up of two trainees engaged in a training environment represented as an industrial control panel simulator on a personal computer, with monitoring of attentional brainwave activity of the trainees.
Figure 4B:
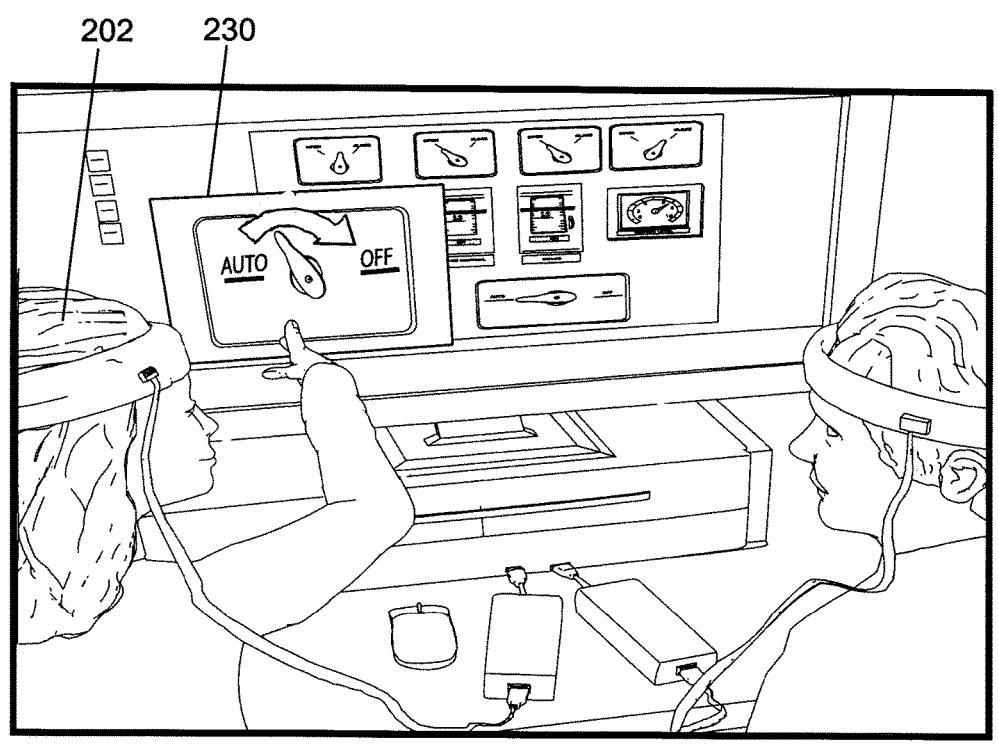
FIG. 4B illustrates an example in a sequence of events, where the trainees in the FIG. 4A training environment are maintaining focused attention states and one of the trainees is selecting an actionable element.
Figure 4C:
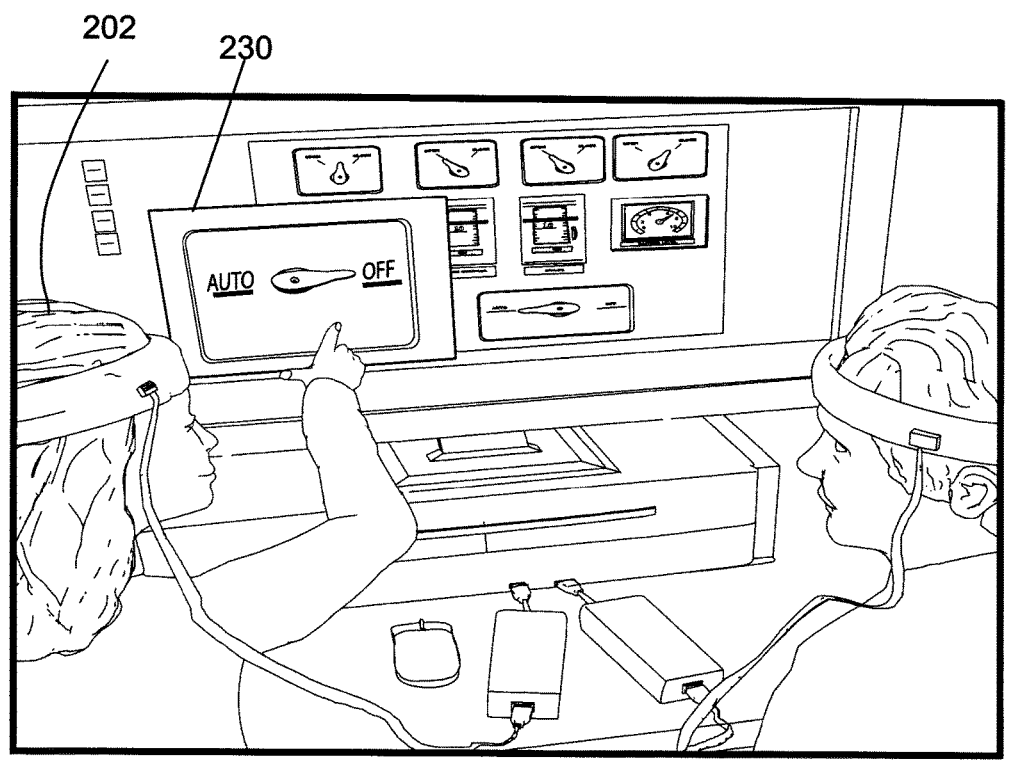
FIG. 4C illustrates a further example in a sequence of events, where the trainees in the FIG. 4A training environment are maintaining focused attention states and one of the trainees is actuating an actionable element.

In FIG. 4A, both trainees 202 and 204 have achieved and are maintaining their individual focused attention states, allowing the training session to proceed. The trainee 202 on the left has selected an actionable element 230 with her finger. In FIG. 4B, the trainee 202 is viewing and actuating an enlarged view of the actionable element 230. As shown in FIG. 4C, the trainee 202 is able to actuate (turn) the actionable element 230.

Figure 4D:
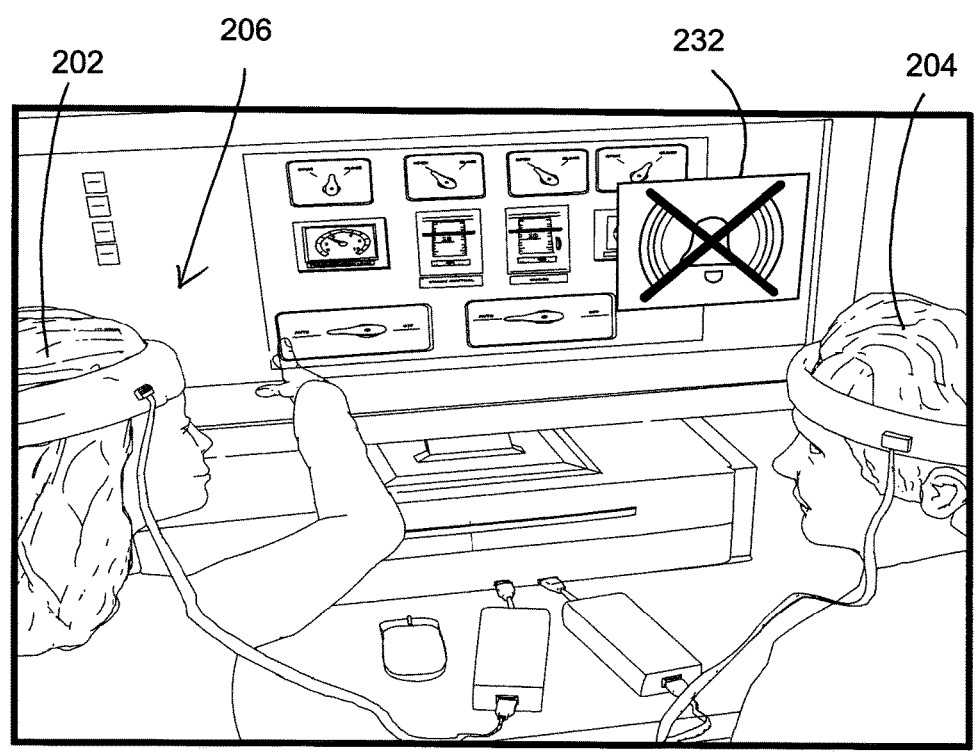
FIG. 4D illustrates a distraction introduced into the FIG. 4A training environment, where the distraction has challenged the trainees to the extent the trainees are no longer both (collectively) in focused attention states.

FIG. 4D illustrates the introduction of a distracter or distraction 232, challenging the focused attention state of the trainees 202 and 204. In FIG. 4D, the distraction is a loud and visible bell 232. In the particular situation illustrated in FIG. 4D, the two trainees 202 and 204 have not both achieved and maintained their individual focused attention states, likely due to the distraction 232, represented by an "X" over the distraction 232. Although the trainee 202 on the left is attempting to select and actuate the actionable element 230 with her finger, because the trainees 202 and 204 collectively are unable to maintain their individual focused attention states, the training environment 206 is not "activated," and the trainee 202 is not able to actuate the actionable element 230 or control with her finger.

Figure 4E:
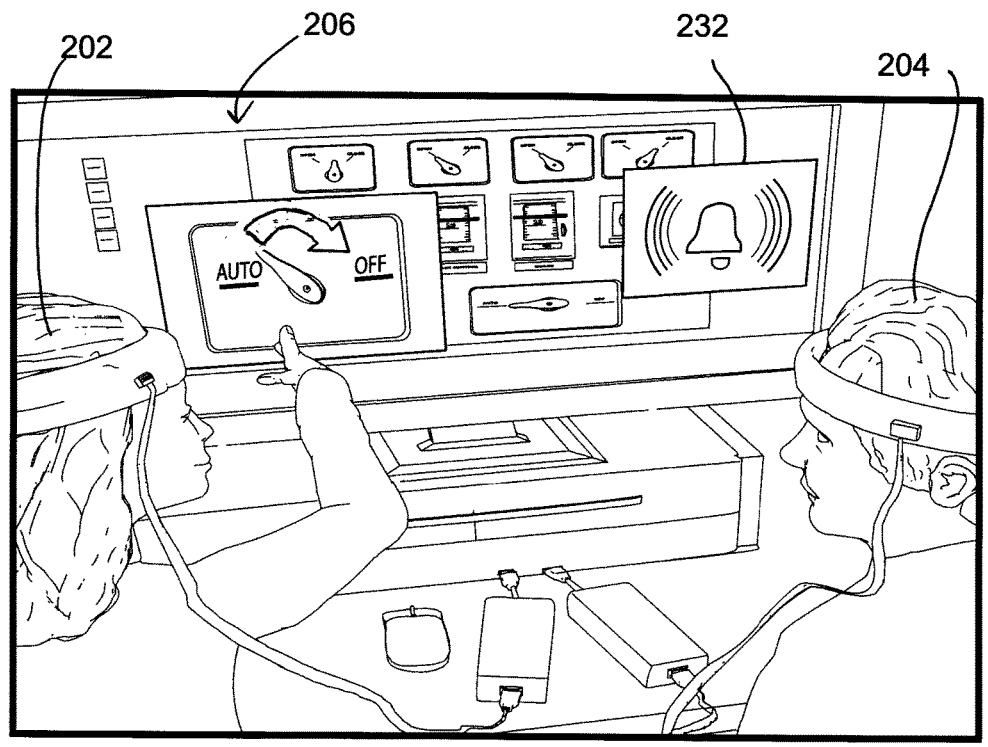
FIG. 4E illustrates a contrasting situation where a distraction is introduced into the FIG. 4A training environment, but both trainees are able to maintain a focused attention state.

FIG. 4E illustrates a contrasting situation. Again depicted on the touch screen computer display 226 is the distraction 232, a loud and visible bell. In FIG. 4E, both trainees 202 and 204 have achieved and are maintaining their individual focused attention states. In other words, the trainees 202 and 204 collectively are able to maintain their individual focused attention states. The training environment 206 is "activated," allowing the training session to proceed. The trainee 202 is able to actuate the actionable element 230 or control with her finger.

Figure 5A:
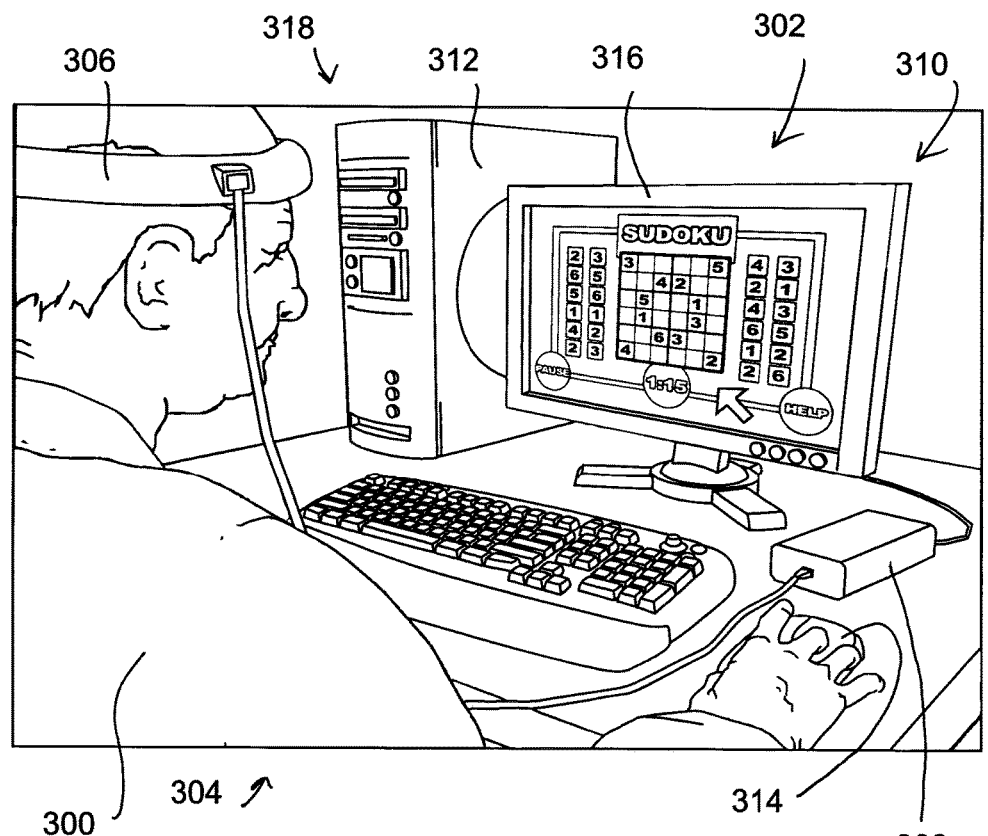
FIG. 5A illustrates an elderly trainee attempting to solve a cognitive puzzle, with monitoring of attentional brainwave activity of the trainee, and where the trainee is not in a focused attention state.
Figure 5B:
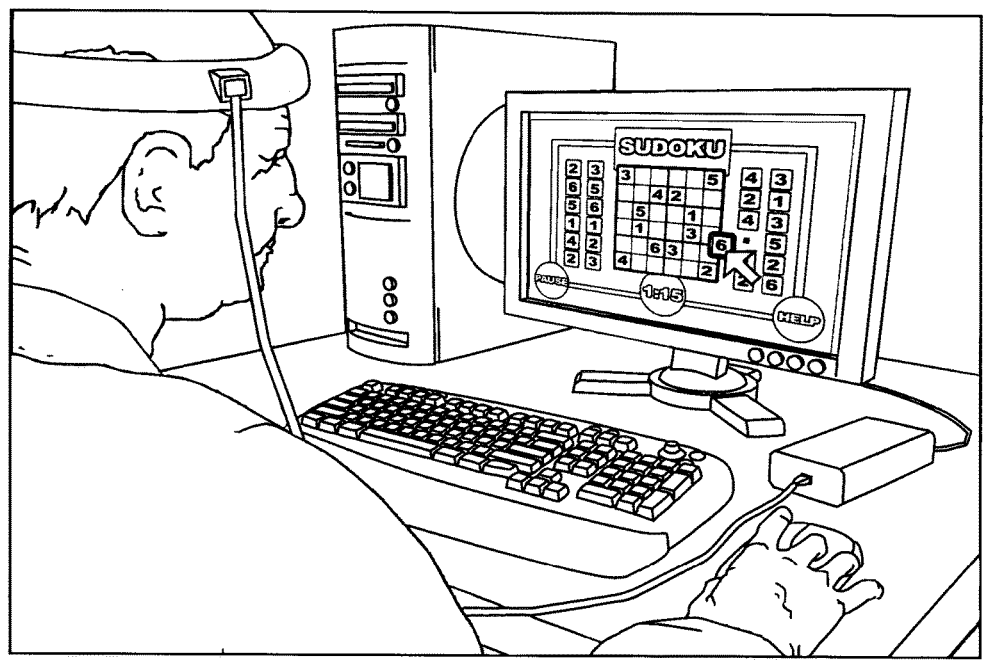
FIG. 5B illustrates an example in a sequence of events where the FIG. 5A trainee is in a focused attention state.

FIGS. 5A and 5B illustrate a trainee 300 shown as a senior citizen 300 engaged in a "brain fitness game" representing a training environment 302 and designed to enhance or restore cognitive abilities. The training environment 302 includes a represented game board and game pieces.

The trainee 300 is using an attentional brainwave monitor 304 which is essentially identical to the attentional brainwave monitor 102 described hereinabove with reference to FIGS. 3A, 3B, 3C, 3D and 3E, and accordingly is not described in detail here. Very briefly, the attentional brainwave monitor 304 includes a sensor headband 306 connected to a brainwave monitoring device hardware unit 308 connected to a desktop computer 310 or personal computer (PC) 310, which includes a CPU unit 312, a mouse 314, and a display 316. The programmed computer 310 implements the "brain fitness game" training environment 302. Implemented within the programmed computer 310 are functions related to the attentional brainwave monitor 304. Also implemented within the programmed computer 310 is an activation device 318 connected to the attentional brainwave monitor 304 and to the training environment 302, and operable to activate the training environment 302 when the determined level of attention of the trainee 300 is at or above a predetermined attention threshold for the trainee 300.

Accordingly, only when the trainee 300 has reached his focused attention state is the training environment 302 "activated" as illustrated in FIG. 5B, allowing the trainee 300 to solve the puzzle using the computer mouse 314. If the trainee 300 loses focus, the training environment 302 goes to an inactive state: the game board and game pieces are displayed, but the trainee 300 cannot select or move the pieces. When the trainee 300 regains his focused attention state, the game board and pieces of the training environment return to the active condition and the trainee 300 can continue to solve the puzzle.

A variation on the activation is making the actual display of the individual game pieces contingent on maintaining a focused attention state. Losing focus causes the pieces to be removed temporarily from the display. Only when the trainee 300 regains a focused attention state are the pieces redisplayed. Another variation is a version for a cognitively-challenged trainee, where the trainee receives hints or directions on the next move contingent on the trainee reaching and maintaining his focused attention state for initially short, and then progressively longer, periods of time.

Figure 6A:
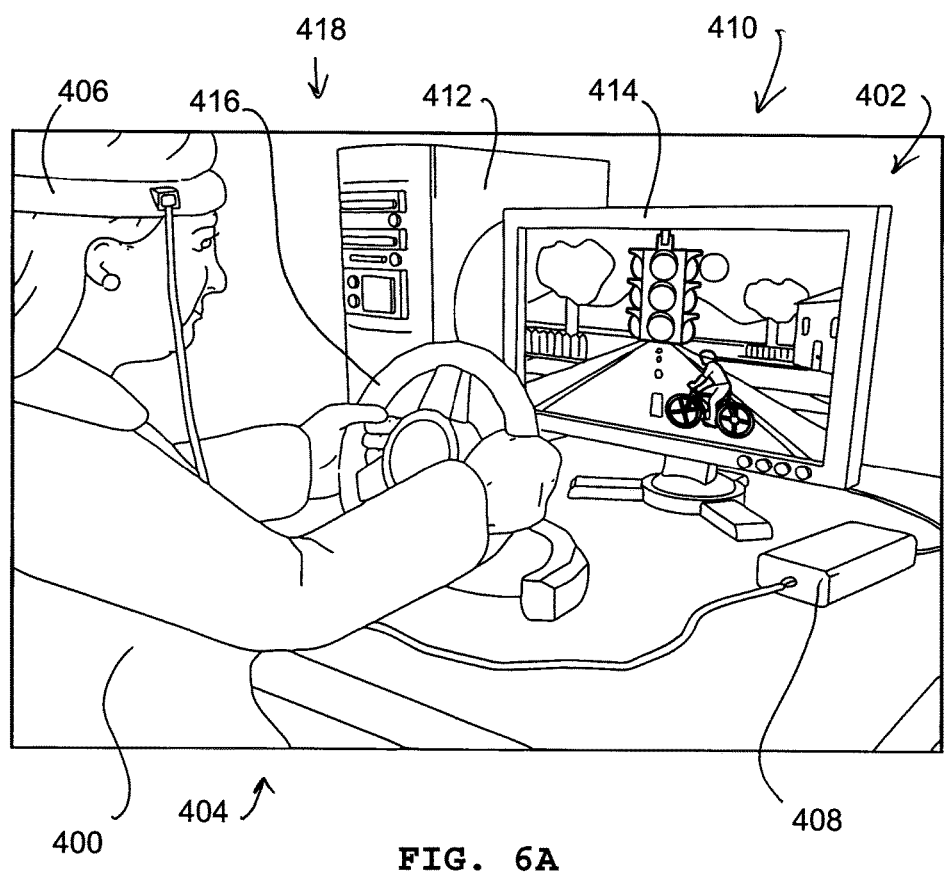
FIG. 6A illustrates an elderly female trainee using a driving simulator, with monitoring of attentional brainwave activity of the trainee, and where the trainee is in a focused attention state.
Figure 6B:
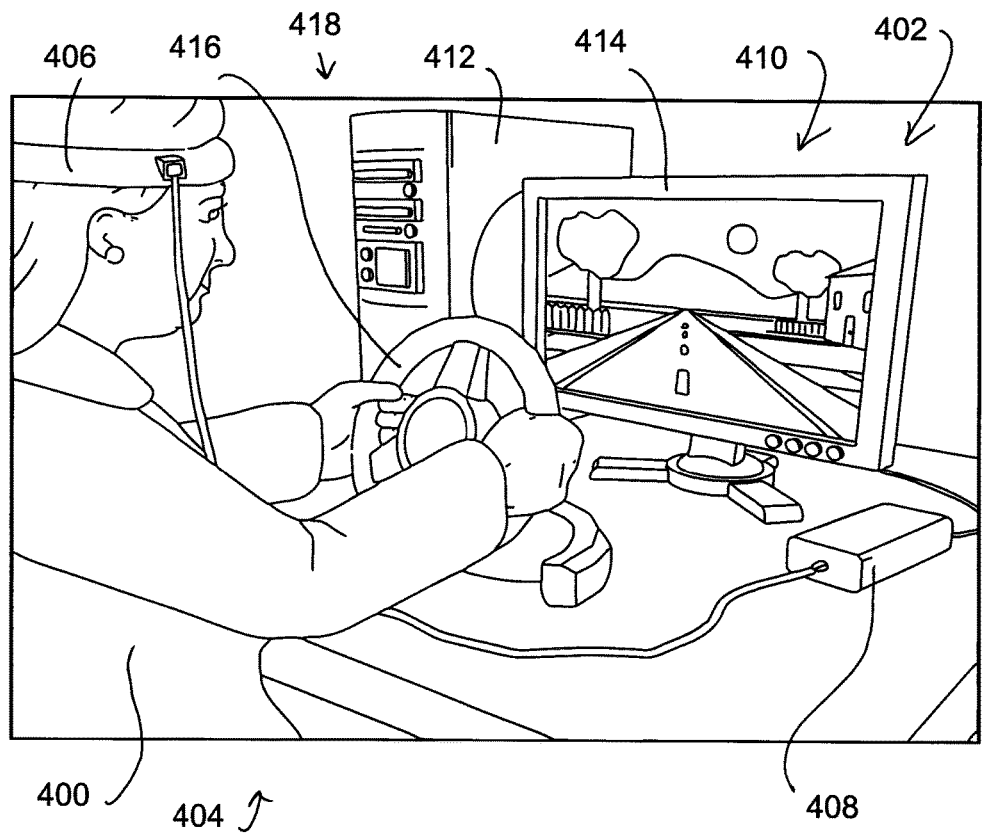
FIG. 6B illustrates an example in a sequence of events where the FIG. 6A trainee is no longer in a focused attention state.

FIGS. 6A and 6B illustrate a trainee 400 shown as a senior citizen 400 in her focused attention state in a training environment 402 in the representative form of a driving simulator 402.

The trainee 400 is using an attentional brainwave monitor 404 which is essentially identical to the attentional brainwave monitor 102 described hereinabove with reference to FIGS. 3A, 3B, 3C, 3D and 3E, and accordingly is not described in detail here. Very briefly, the attentional brainwave monitor 304 includes a sensor headband 406 connected to a brainwave monitoring device hardware unit 408 connected to a desktop computer 410 or personal computer (PC) 410, which includes a CPU unit 412 and a display 414. Also connected to the programmed computer 410 is a steering wheel input device 416. The programmed computer 410 implements the driving simulator 402 training environment 402, via the display 414 and the steering wheel input device 416. Implemented within the programmed computer 410 are functions related to the attentional brainwave monitor 404. Also implemented within the programmed computer 410 is an activation device 418 connected to the attentional brainwave monitor 404 and to the training environment 402, and operable to activate the training environment 402 when the determined level of attention of the trainee 400 is at or above a predetermined attention threshold for the trainee 400.

As shown in FIG. 6B, if the trainee 400 loses her focused attention state, the training environment 402 is inactivated. The trainee 400 is no longer able to interact with the driving simulator 402, and the driving simulator 402 pauses. When the trainee 400 regains her focused attention state, the training environment 402 is again "activated." The driving simulator 404 is restarted, and the trainee 400 is again able to interact with the driving simulator 402

A variation of the training protocol is that the trainee 400 losing her focused attention state results in inability of the trainee 400 to interact with the training environment, but her vehicle continues to roll, causing a traffic violation or accident. Other variations include the introduction of distractions to the trainee 400 to challenge her focused attention state, such as cell phone ringing, sirens, radio noise or flashing lights.

Figure 7:
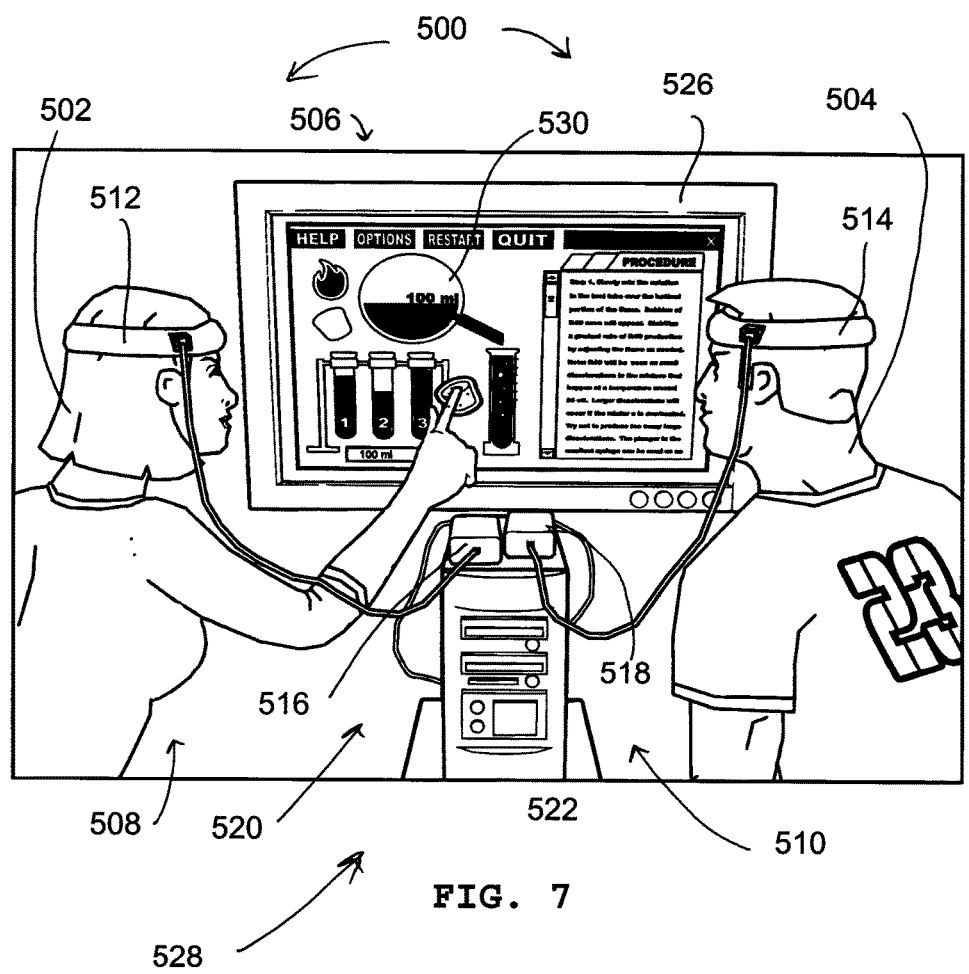
FIG. 7 illustrates a team made up of two trainees represented as chemistry students engaged in a training or learning environment presenting a chemistry lesson on a personal computer, with monitoring of attentional brainwave activity of the student trainees.

FIG. 7 illustrates a team 500 of two trainees 502 and 504 engaged in an interactive chemistry lesson training or learning environment 506. The trainees 502 and 504 are using respective attentional brainwave monitors 508 and 510, each of which is essentially identical to the attentional brainwave monitor 102 described hereinabove with reference to FIGS. 3A, 3B, 3C, 3D and 3E, and accordingly are not described in detail here. Briefly, the attentional brainwave monitors 508 and 510 include respective sensor headbands 512 and 514 connected to respective brainwave monitoring device hardware units 516 and 518. The hardware units 516 and 518 are connected to a single a desktop computer 520 or personal computer (PC) 520, which includes a CPU unit 522 and a touch screen computer display 526. Implemented within the programmed computer 520 are functions related to the attentional brainwave monitors 508 and 510, depending on design considerations for a particular system. Also implemented within the programmed computer 520 is an activation device 528 connected to the attentional brainwave monitors 508 and 510 and to the training environment 506, and operable to activate the training environment 506 when the determined level of attention of all team member trainees 502 and 504 is at or above a predetermined attention threshold for the particular team member trainee 502 or 504.

Accordingly, when all the members 502 and 504 of the team 500 have reached their individual focused attention states, the training environment 506 is activated, allowing the team members 502 and 504 to actuate associated actionable elements 530. In FIG. 7, the actionable elements 530 include beakers and test tubes on the touch screen display 526. When either member 502 or 504 of the team 500 loses focus, the training or learning environment 500 goes to an inactive state, and neither student 502 or 504 is able to actuate actionable elements 530.

Figure 8:
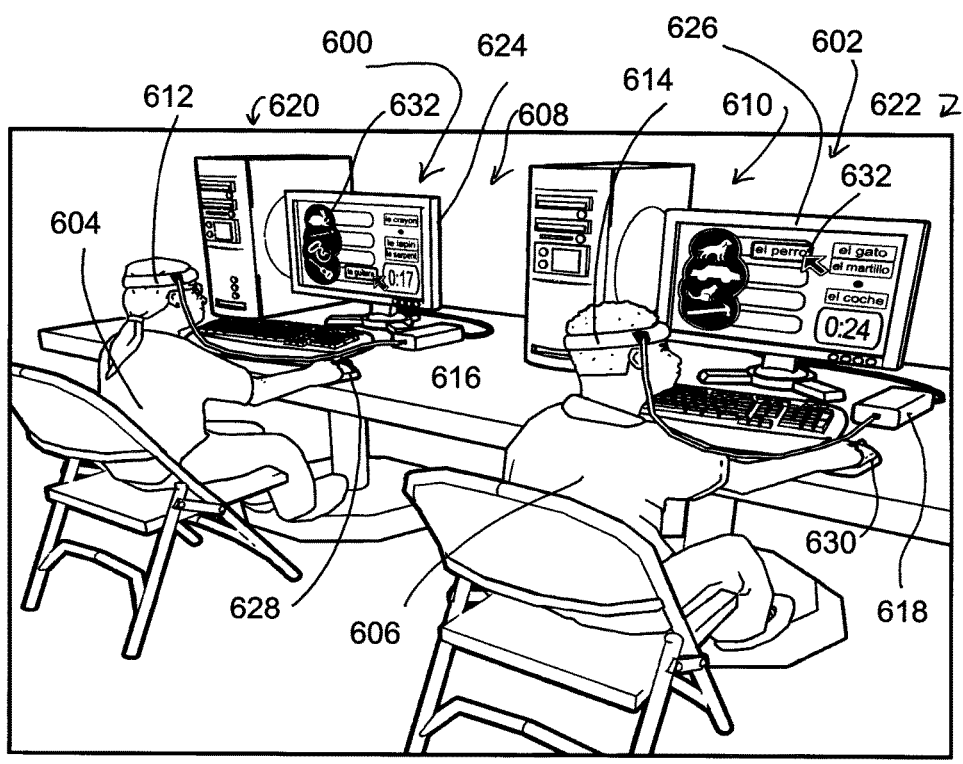
FIG. 8 illustrates a team made up of two trainees represented as foreign language students engaged in a training or learning environment represented as a computer lab electronic foreign language learning environment, with monitoring of attentional brainwave activity of the student trainees.

FIG. 8 illustrates a training environments 600 and 602 in a networked foreign language learning lab 600 with two students 604 and 606 or trainees 604 and 606 interacting with a computerized language lesson. The trainees 604 and 606 are using respective attentional brainwave monitors 608 and 610 essentially the same as those described above, including respective sensor headbands 612 and 614 connected to respective brainwave monitoring device hardware units 616 and 618. The student trainees 604 and 606 are using individual personal computers (PCs) 620 and 622 with individual displays 624 and 626, and individual computer mice 628 and 630.

When either student 604 or 606 has reached his focused attention state as determined by the brainwave monitor 608 or 610, the training or learning environment 600 or 602 for that student 604 or 606 is activated. At that point, the student 604 or 606 can manipulate actionable elements 632, in this example matching foreign words or phrase with the corresponding picture using a mouse 628 or 630 drag and drop operation. If a student 604 or 606 loses focus, the learning environment 600 or 602 goes to an inactive state, and the student 604 or 606 is unable to interact. When a student 604 or 606 regains his focused attention state, the lesson is activated and the ability to interact is restored.

Variations of networked e-learning with attentional brainwave monitoring include intranets, wide area networks and the Internet. Variations also include client-side and server-side administration of the lessons.

Figure 9:
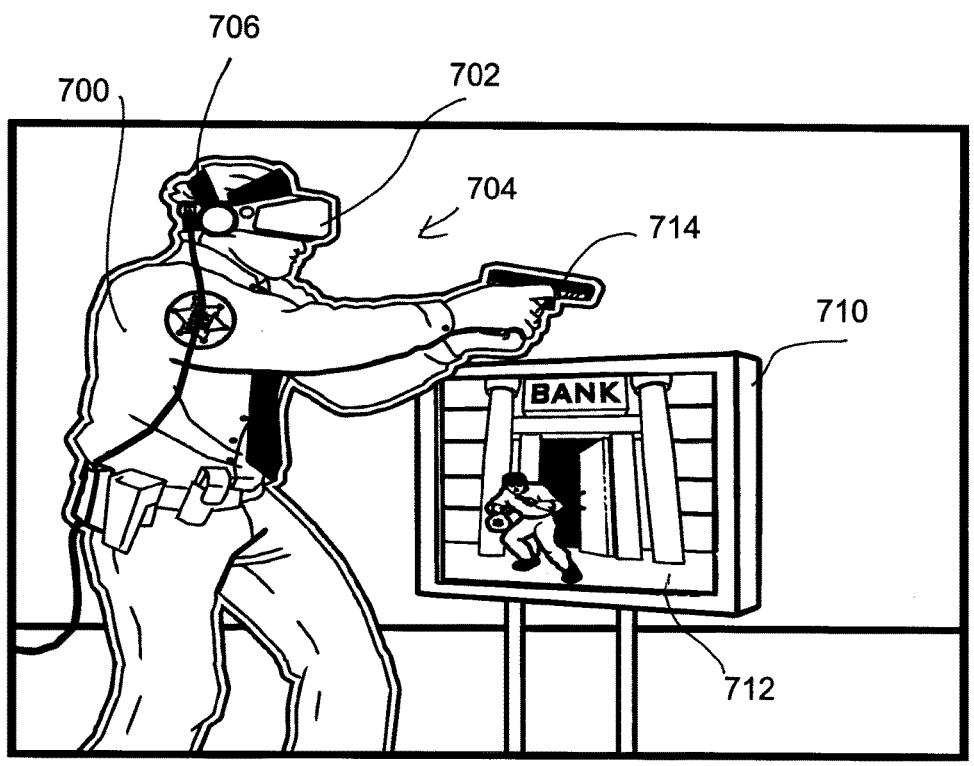
FIG. 9 illustrates a law enforcement officer trainee undergoing training in a virtual reality training environment, with monitoring of attentional brainwave activity of the trainee.

FIG. 9 illustrates a law enforcement officer trainee 700 receiving job training using virtual reality (VR) equipment represented by virtual reality goggles 702, as well as an attentional brainwave monitor 704 represented by a sensor headband 706 integrated with the virtual reality goggles 702. On a flat panel display 710 is a depiction of the scene the trainee 700 is experiencing with his virtual reality goggles 702, representing a training environment 712. When the trainee 700 has reached and maintained a focused attention state, the training environment 712 is activated and the trainee 700 is able interact with the training environment 712. In a variation, the trainee 700 is then permitted to select and actuate actionable elements in the training environment using a laser pointer directed from his gun 714.

Figure 10A:
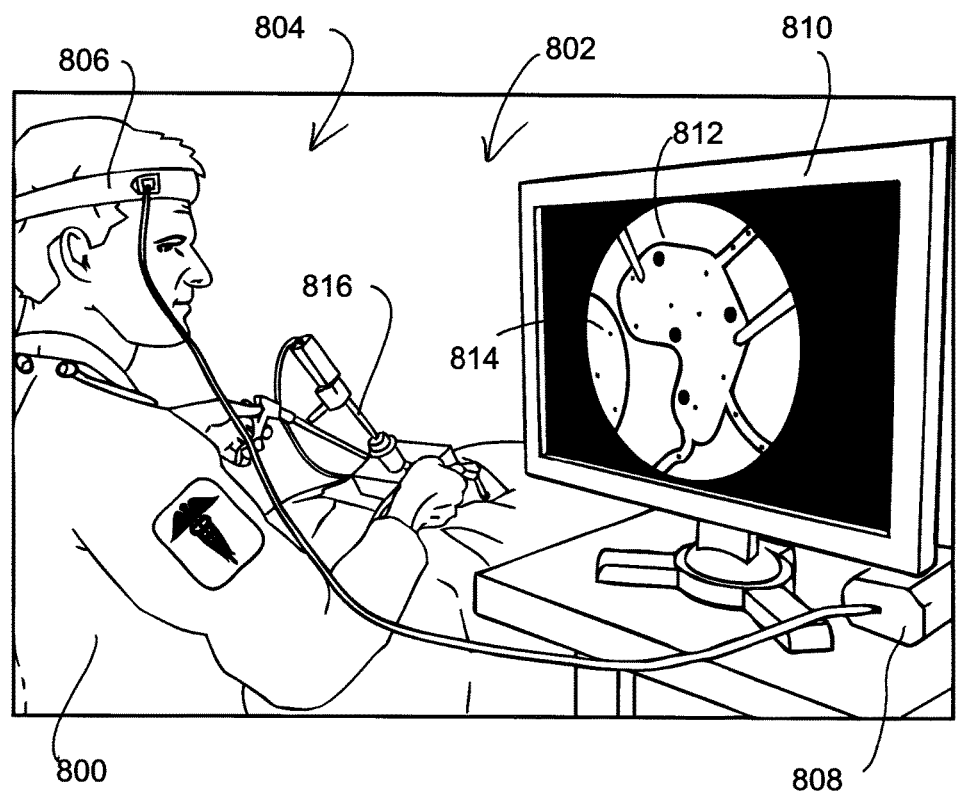
FIG. 10A illustrates a medical professional trainee in a medical simulator training environment, with monitoring of attentional brainwave activity of the trainee.
Figure 10B:
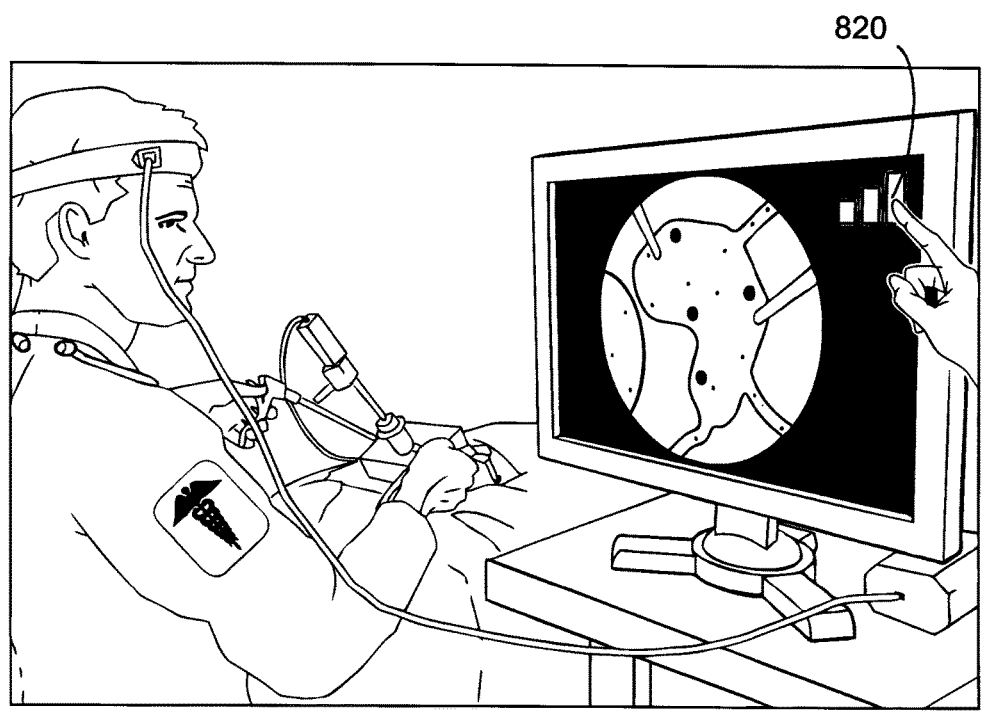
FIG. 10B illustrates an instructor control feature in the medical simulator training environment of FIG. 10A.

FIGS. 10A and 10B illustrate a medical professional trainee 800 interacting with a medical training simulator 802 representing a training environment 802, as well as an attentional brainwave monitor 804 including a sensor headband 806 and a brainwave monitoring device hardware unit 808 attached to a desktop computer represented by a computer monitor 810. As part of the training environment 802, a surgical procedure 812 is represented on the computer monitor 810. The surgical procedure 812 is activated the level of attention of the trainee 800 is at or above a predetermined attentional threshold or baseline, indicating the trainee 800 is in a focused attention state. The trainee 800 is then permitted to select and actuate actionable elements 814 in the training environment 812 using medical simulation tools 816. If the trainee 800 loses his focused attention state, the surgical procedure 812 of the training environment 802 becomes inactive and the trainee 800 is unable to actuate the actionable elements 814.

In FIG. 10B, an additional control feature 820 is included in the training environment 812, and appears in the upper right hand corner of the computer monitor 810 as a series of graduated bars 820. An instructor may touch one of the bars 820 during a training session to increase attentional threshold or baseline which the trainee 800 is required to reach or exceed to be considered in a focused attention state that is needed to maintain activation of the training environment 802 or 812. In this manner, attentional threshold or baseline can be raised in small increments, literally "raising the bar," requiring the trainee 800 to concentrate even more.

Figure 11A:
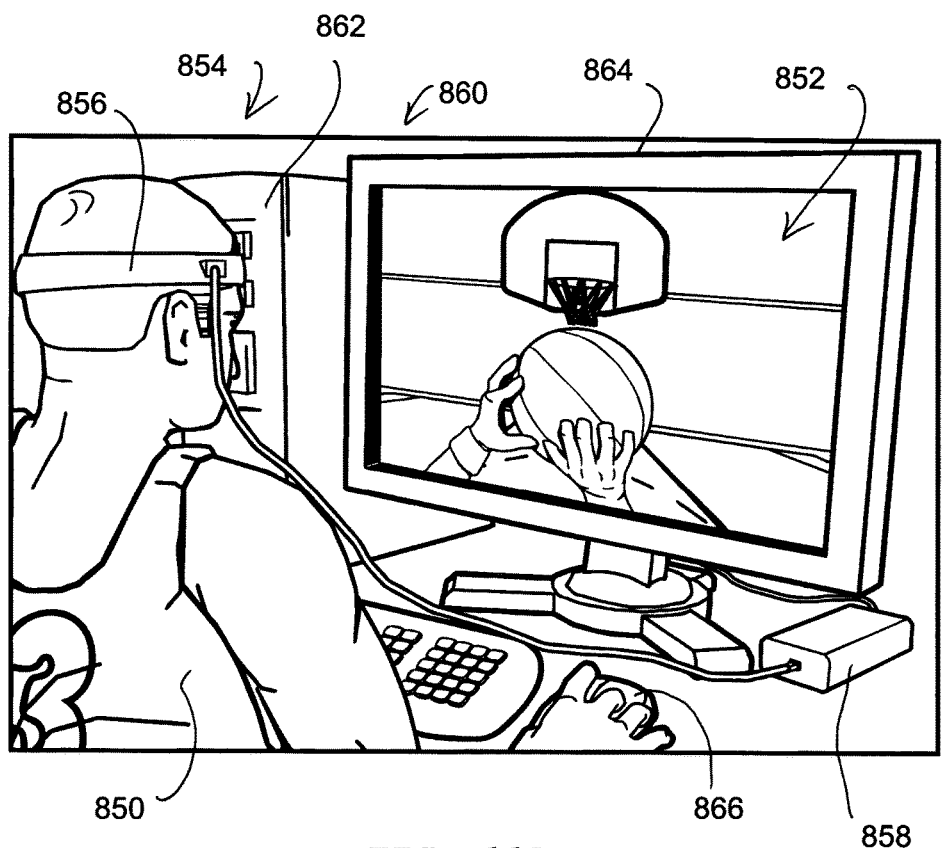
FIG. 11A illustrates a basketball player trainee in a simulated training environment on a personal computer, with monitoring of attentional brainwave activity of the trainee.
Figure 11B:
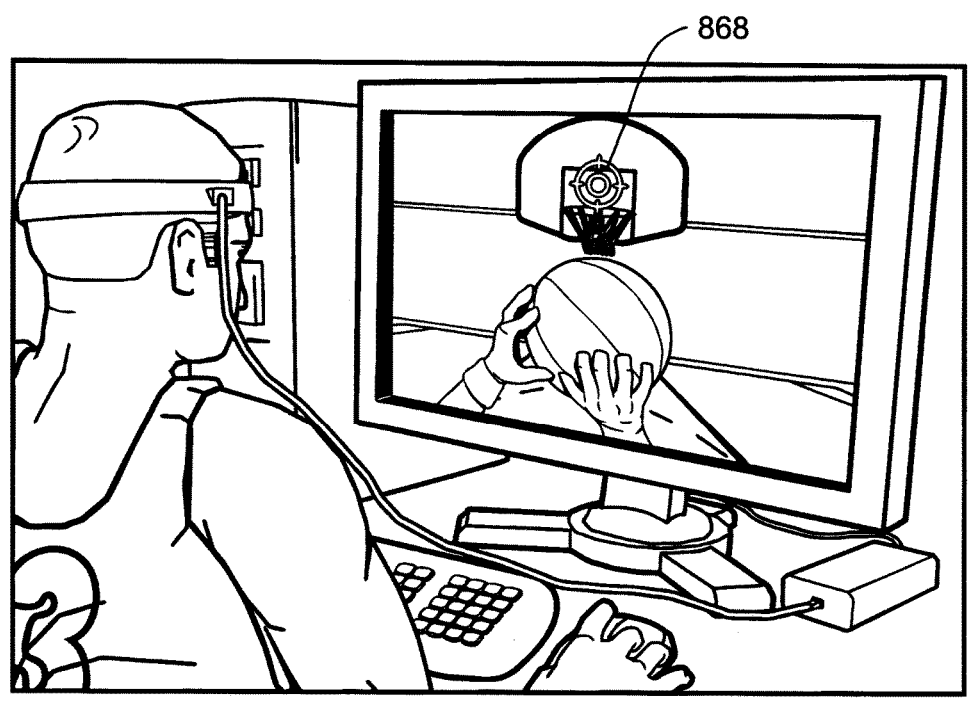
FIG. 11B illustrates an example in a sequence of events where the FIG. 11A trainee is not able to maintain a focused attention state.
Figure 11C:
FIG. 11C illustrates an example in a sequence of events where the FIG. 11A trainee has reached and maintain a focused attention state for a predetermined period of time.

FIGS. 11A, 11B and 11C illustrate a basketball player 850 training in a simulated training environment 852. The trainee 850 is using an attentional brainwave monitor 854 including a sensor headband 856 and a brainwave monitoring device hardware unit 858 attached to a desktop computer 860 including a CPU unit 862, a computer monitor 864, and a mouse 866. The training environment 852 is represented on the computer monitor 864 as a free-throw practice session 852. When the level of attention of the trainee 850 indicates he is in his individual focused attention state, the training environment 852 presents a target selection to the trainee 850 on the computer monitor 864, as represented by the sighted target 868 above the basket hoop in FIG. 11B. In FIG. 1C, the trainee 850 has met and held his focused attention state for a predetermined period of time and is allowed to use an input device, in this scenario the mouse 866, to shoot his basketball successfully.

Figure 12:
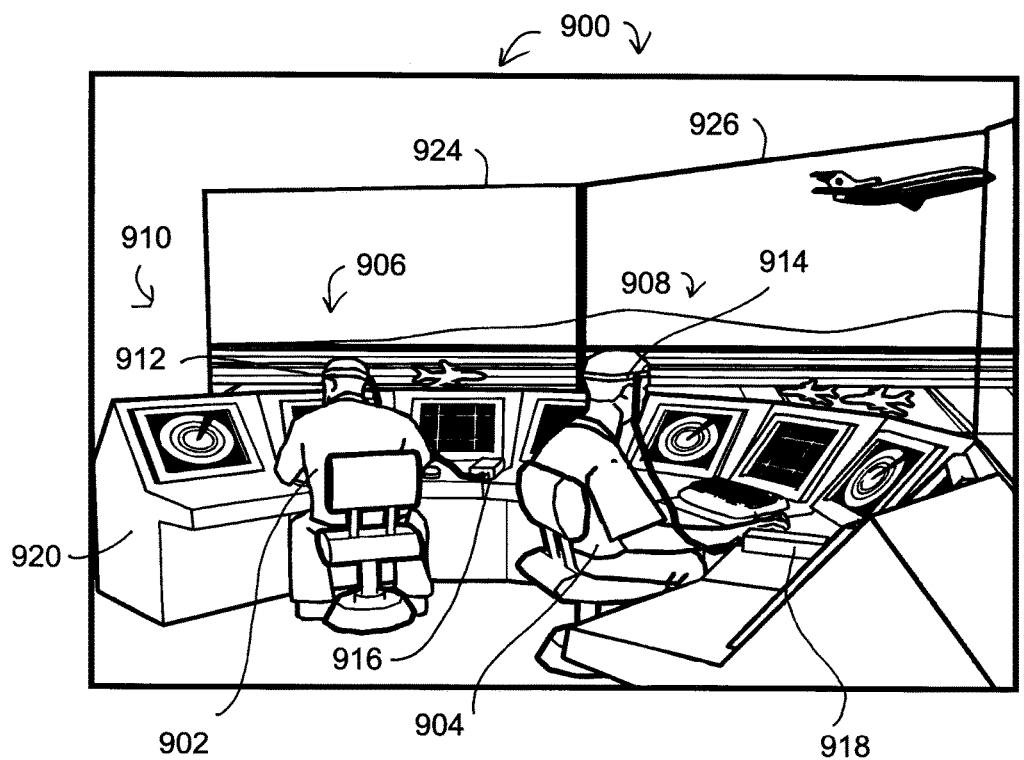
FIG. 12 illustrates a team made up of two air traffic controller trainees engaged in a training environment represented as an air traffic control simulator, with monitoring of attentional brainwave activity of the trainees.

FIG. 12 illustrates a team 900 shown as two air traffic control trainees 902 and 904 equipped with respective attentional brainwave monitors 906 and 908 in a training environment 910 in the form of an air traffic control simulator 910. The attentional brainwave monitors 906 and 908 include respective sensor headbands 912 and 914 and respective brainwave monitoring device hardware units 916 and 918 attached to a simulator controller (not shown). The air traffic control simulator 910 includes both hardwired analog controls/displays and digital controls/displays (collectively designated 920 and 922), two large flat panel computer monitors 924 and 926, and simulator control software. The simulator control software manages all aspects of the training simulator 910, including monitoring the attentional focus of the trainees 902 and 904 via the brainwave monitors 906 and 908. Aspects of the simulation are activated only when the trainees 902 and 904 are in their focused attention state, either individually or collectively depending on the training protocol for the session. If the trainees 902 and 904 fail to reach, or drop out of their focused attention state, the simulator 910 temporarily becomes inactive and the trainees 902 and 904 are unable to select and actuate the analog and digital actionable elements they are responsible for, until they regain focus.

Figure 13A:
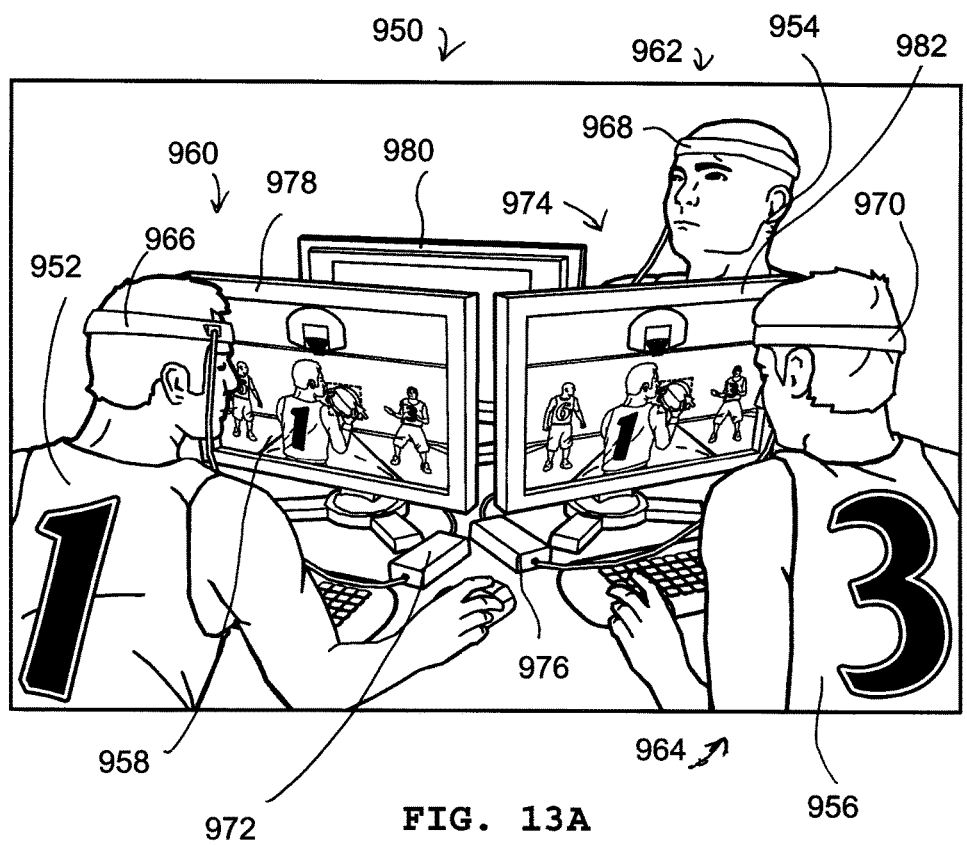
FIG. 13A illustrates a basketball team training in a simulated training environment including individual personal computer monitors, with monitoring of attentional brainwave activity of the team member trainees.
Figure 13B:
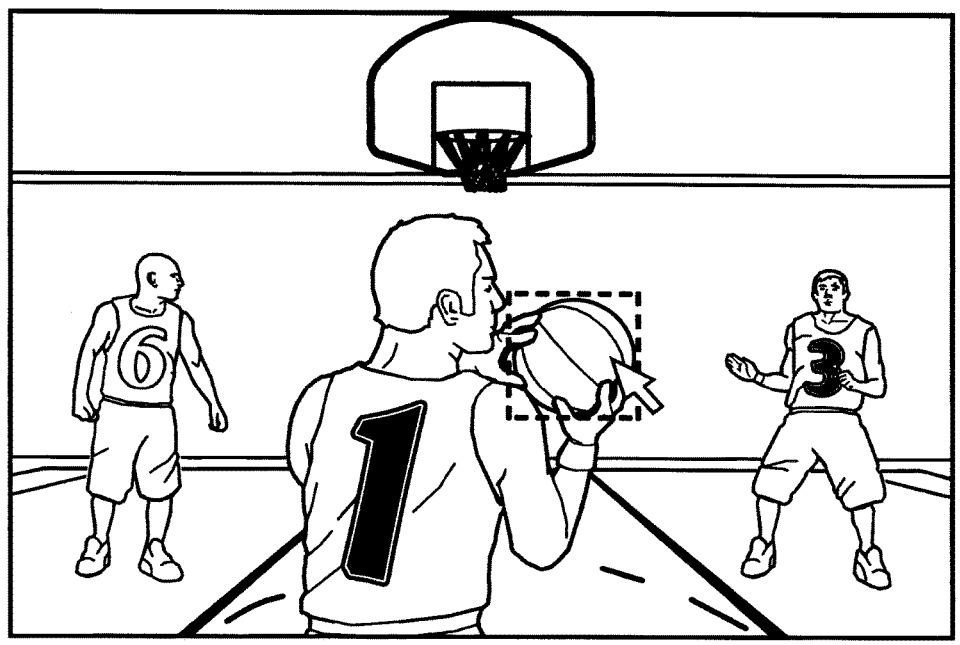
FIG. 13B is an enlarged view of the computer monitor of one of the basketball team member trainees of FIG. 13A.
Figure 13C:
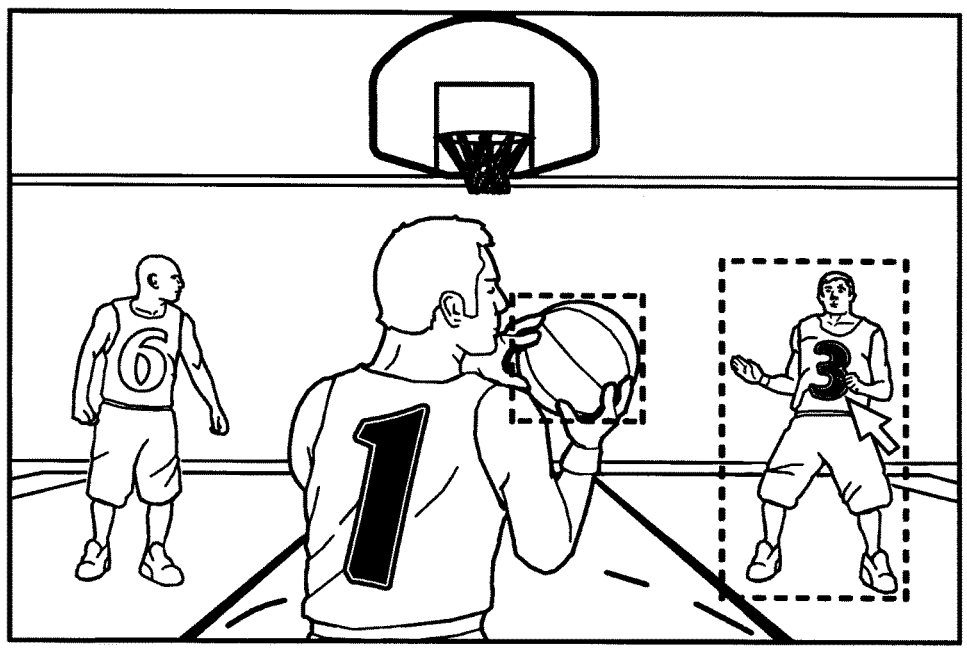
FIG. 13C illustrates an example in a sequence of events in the FIG. 13A training environment.
Figure 13D:
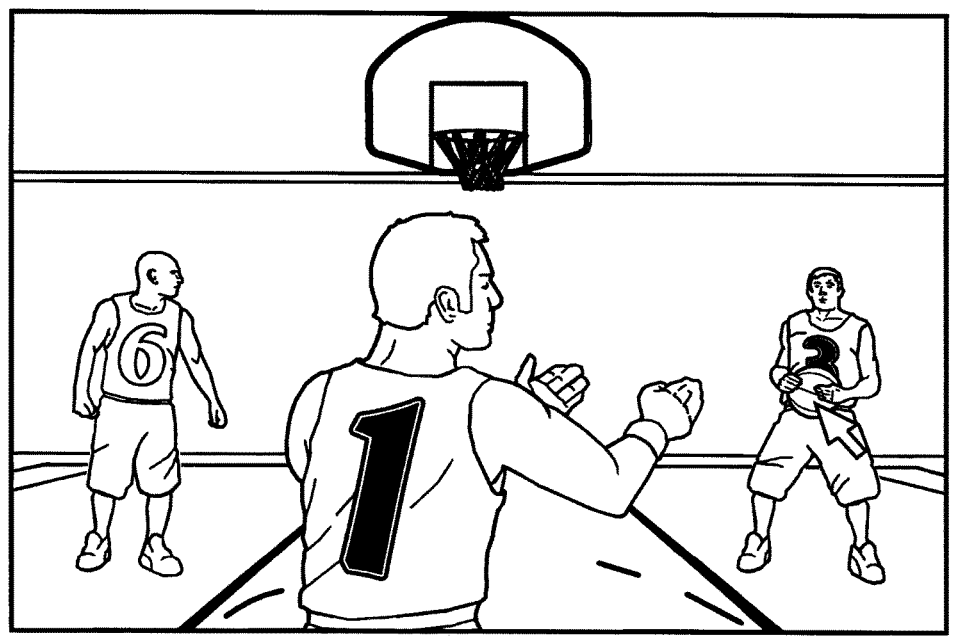
FIG. 13D illustrates another example in a sequence of events in the FIG. 13A training environment.

Finally, FIGS. 13A, 13B, 13C and 13D illustrate a basketball team 950 including individual team members 952, 954 and 956 training in a simulated training environment 958. The trainees 952, 954 and 956 are using respective attentional brainwave monitors 960, 962 and 964 including respective sensor headbands 966, 968 and 970 and respective brainwave monitoring device hardware units 972, 974 and 976 attached to a desktop computer represented by respective computer monitors 978, 980 and 982. The training environment 958 is represented on the computer monitors 978, 980 and 982 as basketball practice session 958. The trainee's jersey number as depicted in the training environment 958 shifts from solid to outline when a trainee's 952, 954 or 956 level of attention is not at or above his predetermined attention threshold as measured by the respective attentional brainwave monitors 960, 962 or 964, and the trainee 952, 954 or 956 is unable to select and/or actuate actionable elements in the training environment 958. Additionally, an inattentive player cannot be selected or actuated by other team members at full attention. A focused attention state is indicated when the trainees' jersey numbers are solid black as depicted in the training environment 958. FIG. 13B is a close-up diagram of the computer monitor display of team member number "1" as depicted in FIG. 13A. The jersey number of team member number "6" has shifted to outline form indicating inattention. Team member number "1" has selected the basketball using an input device as indicated by a bounding marquee and mouse pointer. In FIG. 13C, team member with a jersey #1 has selected the basketball using an input device as indicated by a bounding marquee and mouse pointer and selected the team player number with jersey #3. In FIG. 13D, the team member with a jersey #1 has passed the selected basketball to the selected the team player number with jersey #3 via pressing the right mouse button.

Although the attentional brainwave monitors specifically illustrated herein employ electrodes or sensors attached to the heads of the trainees, the invention may as well be embodied in methods and apparatus which employ electrodes or sensors attached to or proximate portions of the body of a trainee below the head, such as on the arms, legs or back. Such apparatus includes a body-attachment device for securing an amplifier and transmitter unit to a portion of the trainee's body below the head, a wireless receiver, and a programmed computing device for receiving signals from the electrodes or sensors and wirelessly transmitted. Raw signals from the electrodes or sensors are filtered and analyzed to determine the magnitude of brain wave activity within particular frequency bands of interest which are indicative of level of attention. Stated in other words, it has been discovered that attentional brainwave monitors as described herein which include electrodes intended to me attached to the head are also effective for purposes described herein when the electrodes (or other sensors such an non-contact bio-sensors) are attached, for example, to the arms.

While specific embodiments of the invention have been illustrated and described herein, it is realized that numerous modifications and changes will occur to those skilled in the art. It is therefore to be understood that the appended claims are intended to cover all such modifications and changes as fall within the true spirit and scope of the invention.

What is claimed is:

1. An apparatus for training a team including at least two team member trainees, comprising:
   a training environment for teaching a skill beyond merely maintaining a particular brainwave state, said training environment having not-activated and activated states, the trainee not being allowed to proceed in said training environment when said training environment is in the not-activated state, and the trainee being allowed to actively participate in said training environment when said training environment is in the activated state;
   a brainwave monitor for each trainee for monitoring electrical activity within the brain of each trainee, and determining each trainee's level of attention; and
   an activation device connected to said brainwave monitors and to said training environment, and operable to activate said training environment to the activated state when the levels of attention of all team member trainees are simultaneously at or above a predetermined attention threshold.

2. An apparatus for training a team including at least two team member trainees, comprising:

a training environment for teaching a skill beyond merely maintaining a particular brainwave state, said training environment having not-activated and activated states, the trainee not being allowed to proceed in said training environment when said training environment is in the not-activated state, and the trainee being allowed to actively participate in said training environment when said training environment is in the activated state;

a brainwave monitor for each trainee for monitoring electrical activity within the brain of each trainee, and determining each trainee's level of attention; and an activation device connected to said brainwave monitors and to said training environment, and operable to activate said training environment to the activated state when the level of attention of each team member trainee is simultaneously at or above a predetermined attention threshold for the particular team member trainee, which is the attention baseline for the particular team member trainee.

3. A training method for training a team including at least two team member trainees, comprising:

providing an apparatus for training a team including at least two team member trainees according to claim 1;

employing brainwave monitors of the apparatus for determining the level of attention for each team member trainee;

providing a training environment from the apparatus for teaching a skill beyond merely maintaining a particular brainwave state, said training environment having not-activated and activated states, the trainee not being allowed to proceed in said training environment when said training environment is in the not-activated state, and the trainee being allowed to actively participate in said training environment when said training environment is in the activated state; and monitoring the levels of attention of the team member trainees and activating the training environment of the apparatus to the activated state when the levels of attention of all team member trainees are simultaneously at or above a predetermined attention threshold.

4. A training method for training a team including at least two team member trainees, comprising:

providing an apparatus for training a team including at least two team member trainees according to claim 2;

employing brainwave monitors of the apparatus for determining level of attention for each team member trainee;

providing a training environment from the apparatus for teaching a skill beyond merely maintaining a particular brainwave state, said training environment having not-activated and activated states, the trainee not being allowed to proceed in said training environment when said training environment is in the not-activated state, and the trainee being allowed to actively participate in said training environment when said training environment is in the activated state; and monitoring the levels of attention of the team member trainees and activating the training environment to the activated state of the apparatus when the level of attention of each team member trainee is simultaneously at or above a predetermined attention threshold for the particular team member trainee, which is the attention baseline for the particular team member trainee.

* * * * *